(12) United States Patent
Tracey et al.

(10) Patent No.: US 11,541,239 B2
(45) Date of Patent: *Jan. 3, 2023

(54) NERVE STIMULATION FOR TREATMENT OF DISEASES AND DISORDERS

(71) Applicant: THE FEINSTEIN INSTITUTES FOR MEDICAL RESEARCH, Manhasset, NY (US)

(72) Inventors: Kevin J. Tracey, Old Greenwich, CT (US); Sangeeta S. Chavan, Syosset, NY (US)

(73) Assignee: The Feinstein Institutes for Medical Research, Manhasset, NY (US)

( * ) Notice: Subject to any disclaimer, the term of this patent is extended or adjusted under 35 U.S.C. 154(b) by 316 days.

This patent is subject to a terminal disclaimer.

(21) Appl. No.: 16/695,557

(22) Filed: Nov. 26, 2019

(65) Prior Publication Data

US 2020/0101293 A1 Apr. 2, 2020

Related U.S. Application Data

(63) Continuation of application No. 15/677,080, filed on Aug. 15, 2017, now Pat. No. 10,507,327, which is a
(Continued)

(51) Int. Cl.
*A61N 1/36* (2006.01)

(52) U.S. Cl.
CPC ..... *A61N 1/36135* (2013.01); *A61N 1/36002* (2017.08); *A61N 1/36007* (2013.01); *A61N 1/36053* (2013.01); *A61N 1/36071* (2013.01)

(58) Field of Classification Search
CPC ............ A61N 1/36135; A61N 1/36002; A61N 1/36007; A61N 1/36053; A61N 1/36071
See application file for complete search history.

(56) References Cited

U.S. PATENT DOCUMENTS 5,231,988 A * 8/1993 Wernicke ........... A61N 1/36053
600/319
9,211,409 B2 12/2015 Tracey et al.
(Continued)

FOREIGN PATENT DOCUMENTS

| WO | 93/02743 A1 | 2/1993 |
| WO | 2014169145 A1 | 10/2014 |
| WO | 2016134197 A1 | 8/2016 |

OTHER PUBLICATIONS

PCT International Search Report and Written Opinion dated May 23, 2016 for PCT International Patent Application No. PCT/US2016/18573, 15 pages.
(Continued)

*Primary Examiner* — Catherine M Voorhees
*Assistant Examiner* — Roland Dinga
(74) *Attorney, Agent, or Firm* — Amster, Rothstein & Ebenstein LLP

(57) ABSTRACT

Methods are disclosed for treating a subject having a disease or disorder comprising stimulating a nerve of the subject with a corrective stimulus pattern derived from a disease-specific, condition-specific, endogenous mediator-specific or pharmacologic agent-specific neurogram in an amount and manner effective to treat the disease or disorder.

19 Claims, 26 Drawing Sheets

Related U.S. Application Data continuation-in-part of application No. PCT/US2016/018573, filed on Feb. 19, 2016.

(60) Provisional application No. 62/118,700, filed on Feb. 20, 2015, provisional application No. 62/237,041, filed on Oct. 5, 2015, provisional application No. 62/237,047, filed on Oct. 5, 2015.

(56) References Cited

U.S. PATENT DOCUMENTS

| | | | |
|---|---|---|---|
| 9,662,490 | B2 | 5/2017 | Tracey et al. |
| 10,166,395 | B2 | 1/2019 | Tracey et al. |
| 10,507,327 | B2 * | 12/2019 | Tracey ............... A61N 1/36135 |
| 2007/0027484 | A1 | 2/2007 | Guzman et al. |
| 2009/0247934 | A1 | 10/2009 | Tracey et al. |
| 2009/0254143 | A1 | 10/2009 | Tweden et al. |
| 2011/0118810 | A1 | 5/2011 | Cowan et al. |
| 2011/0319969 | A1 | 12/2011 | Dobak, III |
| 2013/0079745 | A1 | 3/2013 | Thornton et al. |
| 2014/0228900 | A1 * | 8/2014 | Osorio ............... A61N 1/36082 607/3 |
| 2016/0067497 | A1 | 3/2016 | Levine et al. |
| 2016/0250097 | A9 | 9/2016 | Tracey et al. |
| 2017/0021174 | A1 | 1/2017 | Thornton et al. |
| 2018/0021214 | A1 | 1/2018 | Tracey et al. |
| 2019/0247659 | A1 | 8/2019 | Kressel et al. |

OTHER PUBLICATIONS

Steinberg B E et al., entitled "Pro- and Anti-inflammatory Cytokines Differentially Activate the Sensory Vagus Nerve," American Society of Anesthesiologists, Abstract, Oct. 14, 2014, 1 page.

Andersson U et al., entitled "Reflex Principles of Immunological Homeostasis," Annu. Rev. Immunol., 2012, 30:313-35. Epub Jan. 6, 2012.

Andersson U et al., entitled "Neural reflexes in inflammation and immunity," J. Exp. Med. vol. 209, No. 6, pp. 1057-1068, 2012.

Borovikova L V et al., entitled "Vagus nerve stimulation attenuates the systemic inflammatory response to endotoxin," Nature, vol. 405, May 25, 2000, pp. 458-462.

Famm K et al., entitled "A jump-start for electroceuticals," Nature, vol. 496, Apr. 11, 2013, pp. 159-161.

Koopman F A entitled "Vague nerve stimulation inhibits cytokine production and attenuates disease severity in rheumatoid arthritis," PNAS, vol. 113, No. 29, 8284-8289, doi: 10.1073/pnas.1605635113, www.pnas.org/cgi/doi/10.1073/pnas.1605635113. Epub Jul. 5, 2016.

Olofsson P S et al., entitled "Single-Pulse and Unidirectional Electrical Activation of the Cervical Vagus Nerve Reduces Tumor Necrosis Factor in Endotoxemia," Bioelectron Med 2:37-42, 2015, pp. 37-42.

Behar M, entitled "Can the Nervous System Be Hacked?" The New York Times Magazine, The Health Issue, May 25, 2014, 7 pages.

Communication Supplementary European Search Report dated Jun. 29, 2018 in connection with European Patent Application No. 16753098.9.

Examination Report No. 1 dated Nov. 29, 2019 from Australian Patent Application No. 2016219951.

* cited by examiner

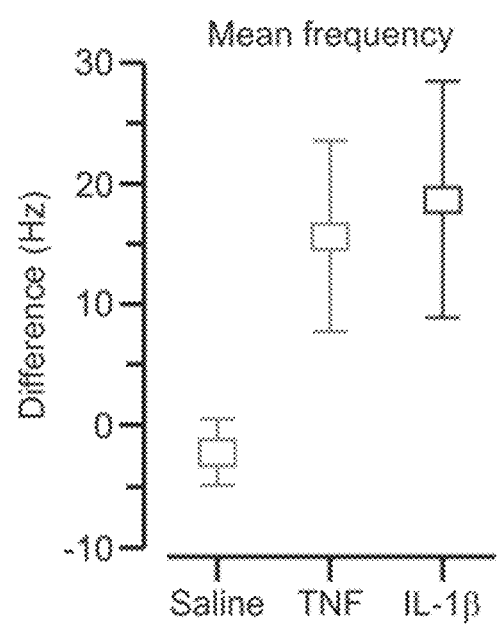
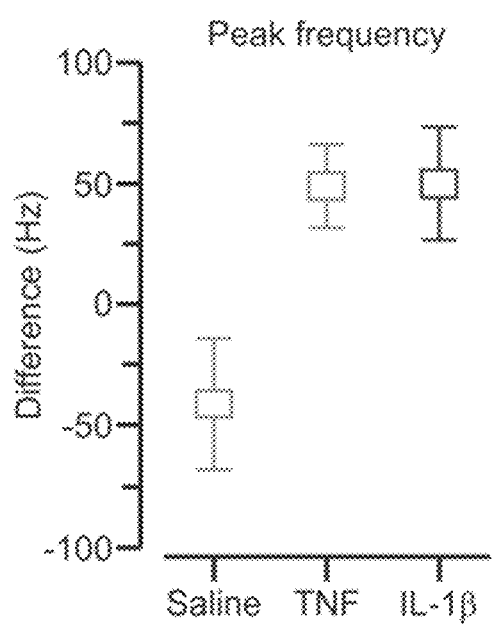
FIG. 4A
FIG. 4B
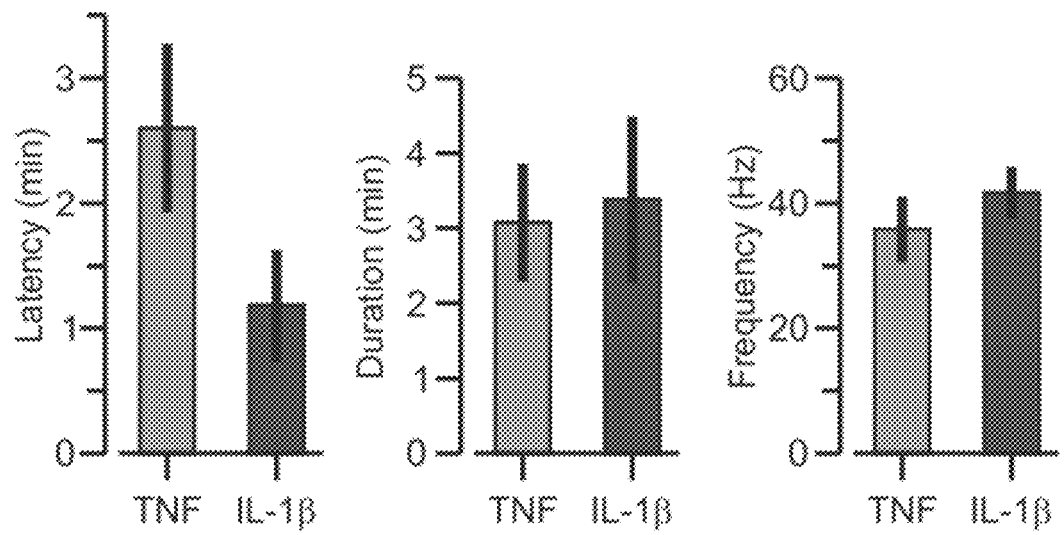
FIG. 4C

NERVE STIMULATION FOR TREATMENT OF DISEASES AND DISORDERS

CROSS-REFERENCE TO RELATED APPLICATIONS

This application is a continuation of U.S. patent application Ser. No. 15/677,080, filed Aug. 15, 2017, now U.S. Pat. No. 10,507,327 B2, issued on Dec. 17, 2019, which is a continuation-in-part of and claims priority of PCT International Patent Application No. PCT/US2016/018573, filed Feb. 19, 2016, which designates the United States of America and which claims the benefit of U.S. Provisional Patent Application No. 62/118,700, filed on Feb. 20, 2015, U.S. Provisional Patent Application No. 62/237,041 filed on Oct. 5, 2015, and U.S. Provisional Patent Application No. 62/237,047 filed on Oct. 5, 2015, the contents of which are herein incorporated by reference into the subject application.

STATEMENT OF GOVERNMENT SUPPORT

This invention was made with government support under grant number W911NF-09-1-0125 awarded by the Defense Advanced Research Projects Agency (DARPA). The government has certain rights in the invention.

BACKGROUND OF THE INVENTION

Throughout this application various publications are referred to in parentheses. Full citations for these references may be found at the end of the specification. The disclosures of these publications are hereby incorporated by reference in their entirety into the subject application to more fully describe the art to which the subject invention pertains.

The nervous system developed over evolutionary time to optimize survival in response to signals from the internal and external environment. In mammals, chemical, mechanical, and electromagnetic signals are sensed by neurons, which propagate action potentials to the central nervous system (CNS). These comprise the afferent arcs of reflex circuits that maintain the body's homeostasis. This fundamental principle of sensing environmental changes in order to mount appropriate reflex responses is central to the physiological mechanisms that allow for not only homeostasis but adaptability and species survival.

Thirty years ago, it was discovered that products of the immune system, including cytokines and other mediators, could be sensed by the nervous system, prompting the suggestion that the immune system could serve as a functional sensory modality (1). In this context, foreign invaders, microbial products, and other exogenous immune stimulators culminate in the release of cytokines. These immune products can in turn interact with the peripheral nervous system and the CNS to elicit neurophysiological responses; however, the question remains whether the sensory neural signals are encoded in cytokine-specific patterns.

There has been an expanding body of knowledge delineating the extensive interface between the nervous and immune systems. Similar to the neural control of the body's general physiological and metabolic states, systemic inflammatory pathways can be modulated by the CNS, with the archetypal pathway being the inflammatory reflex of the vagus nerve (VN) (2). In its efferent arc, electrical signals move down the vagus nerve to the celiac ganglion from which the splenic nerve further propagates the signal towards the spleen. Within the spleen, a specialized subset of T lymphocytes completes the link between the nervous and immune systems (3, 4). Acetylcholine, which is released by these T cells, down-regulates cytokine production by resident macrophage populations thereby producing a systemic anti-inflammatory effect (3).

In contrast to the well-mapped motor arc, the afferent arc remains incompletely understood. Notably, the vagus nerve is primarily sensory, such that numerous afferent signals regarding physiological status travel the vagus nerve from the periphery into the CNS. Oftentimes neglected is the notion that these signals might include the inflammatory status of the animal. The pioneering work by Niijima and collaborators (5-7) led them to postulate that IL-1β might activate peripheral afferents of the vagus nerve that would signal to the CNS about the presence of this cytokine. Physiological studies have shown that an intact vagus nerve is required for a pyrexia response to intra-abdominal IL-1β administration, further corroborating the notion that the vagus nerve might be a primary peripheral inflammation sensor for the CNS (8, 9). Parallel studies in isolated sensory neurons show that neurons express a variety of cytokine receptors, such as the TNF and IL-1β receptors, and are able to change their activation thresholds when exposed to the corresponding exogenous cytokines (10-12). In combination, these studies suggest that the vagus nerve is an important substrate for a peripheral neural network capable of capturing real-time signals pertaining to changes in peripheral inflammatory and immune states.

The present invention addresses the need for improved methods for treating diseases and disorders, in particular methods that do not require administration of drugs to a subject. The methods disclosed herein use a stimulus pattern derived from a disease-specific or condition-specific or endogenous mediator-specific or pharmacologic agent-specific neurogram to produce a stimulus pattern that is applied to a nerve such as the vagus nerve to treat the disease or disorder.

SUMMARY OF THE INVENTION

The present invention provides methods for treating a subject having a disease or disorder comprising stimulating a nerve of the subject with a corrective stimulus pattern derived from a disease-specific or condition-specific or endogenous mediator-specific or pharmacologic agent-specific neurogram in an amount and manner effective to treat the disease or disorder.

As an example, the invention provides methods for treating a subject having inflammation, hypoglycemia or hyperglycemia comprising electrically stimulating a cervical vagus nerve of the subject with a corrective stimulus pattern derived from a disease-specific or condition-specific or endogenous mediator-specific or pharmacologic agent-specific vagus nerve neurogram in an amount and manner effective to treat inflammation, hypoglycemia or hyperglycemia.

Also provided are methods for generating a corrective stimulus for the treatment of a disease or condition, comprising the steps of: providing a disease-specific, condition-specific, endogenous mediator-specific or pharmacologic agent-specific neurogram, and generating a corrective neural stimulus based therefrom.

Figure 1A:
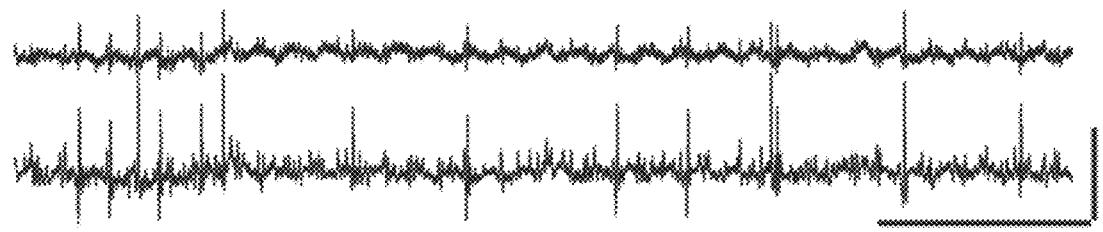
FIG. 1A-1D. Recording vagus nerve compound action potentials. (A) Simultaneous recordings (2 of 3 electrodes are shown) of spontaneous activity in the vagus nerve (VN).

(B) Left, vagus nerve excitation by KCl (4 mM, gray box) applied to the surgical field. Right, Top, period of quiescent activity before KCl (marked by i). Middle, period of intense spiking during KCl (marked by ii). Line indicates the adaptive threshold used to detect compound action potentials (CAPs). Bottom, identified CAPs are aligned with the trace above. (C) Inset, evoked CAPs are obtained by brief electrical pulses that stimulate the vagus nerve. The graph shows the CAP area (mean±SD), which becomes larger with increasing stimulation intensity (pre circles). Lidocaine (2%) largely blocks the evoked CAPs (post circles). (D) Inset, evoked CAPs previous to treatment with tetrodotoxin (100 µM). The graph shows the CAP area (mean±SD) which is completely blocked by the drug. Scale bars (x, y), A, 100 ms, 100 µV; B left, 1 sec, 20 µV; B right, 10 ms, 20 µV; C, D, 2 ms, 40 µV.

FIG. 2A-2E. Afferent fibers of the vagus nerve carry TNF-induced neurograms. (A) Top, trace showing the spontaneous activity of the cervical vagus nerve. Bottom, trace showing the activity of the cervical vagus nerve after peripheral injection of TNF (dose of 50 µg, marked by arrow). (B) Graph depicting the frequency of CAP firing for the control and TNF-induced neurograms (shown in A). The 10-min period immediately after TNF injection is used to calculate the frequency of CAP firing, as well as the equivalent period from the baseline. (C) Diagrams of the surgical vagotomies employed to test the direction of flow of the TNF-induced neurogram. A proximal (Prox.) transection, between the electrodes and the brain, isolates the afferent component, while a distal transection isolates the efferent arm. (D) Graph showing the frequency of CAP firing in 60-sec bins (mean±SEM, line±shaded area) starting 10 min prior to TNF injection (dose of 50 µg) at time zero. Data represent N=3 for each of proximal (filled circles) and distal (open circles) vagotomies. (E) Plot showing CAP frequencies (mean±SEM) for the 10-min periods before and right after TNF in individual mice. The distal transection completely abolishes the TNF effect, which is not affected by the proximal transection (P=0.03 for post values, t test), indicating that afferent fibers are required.

FIG. 3A-3E. Time course for TNF and IL-1β mediated neurograms. (A) Top, trace showing the vagus nerve activity under vehicle (200 µL of sterile saline, marked by arrow), which is used as control. Bottom, graph describing the frequency of CAP firing (mean±SEM, grey area) for N=5 mice, starting 10 min prior to saline injection. (B) Top, representative neurogram for TNF (dose of 50 µg, marked by arrow). Bottom, graph showing the mean frequency±SEM (blue area) for N=6 mice. (C) Top, representative neurogram for IL-1β (dose of 350 ng, marked by arrow). Bottom, graph showing the mean frequency±SEM (green area) for N=8 mice. (D) Plot depicting the frequency of CAP firing (mean±SEM) for TNF at low dose (5 µg, N=6) and high dose (50 µg, N=6). 'Pre' refers to the 30-sec interval just before injection, and 'Post' to the 30-sec interval 5 min post-injection. (E) Plot depicting the frequency of CAP firing (mean±SEM) for IL-1β at low dose (35 ng, N=8) and high dose (350 ng, N=8). 'Pre' refers to the 30-sec period just before injection, and 'Post' to the 30-sec period 2.5 min post-injection.

FIG. 4A-4C. Time domain analysis of TNF and IL-1β mediated neurograms. (A) Boxplot showing the difference (post-injection minus pre-injection) in mean CAP frequency. For TNF (N=6) and saline (N=5), 10-min intervals were used. For IL-1β (N=8), 5-min intervals were used. (B) Boxplot showing the difference in peak CAP frequency. (C) Left, graph depicting the latency (mean±SEM) for the TNF and IL-1β responses. The former is mildly slower than the latter (P=0.043, t test). Middle, graph showing the duration (mean±SEM) of the neurograms induced by TNF and IL-1β. Right, graph presenting the CAP frequency (mean±SEM) of the TNF and IL-1β responses.

Figure 5A:
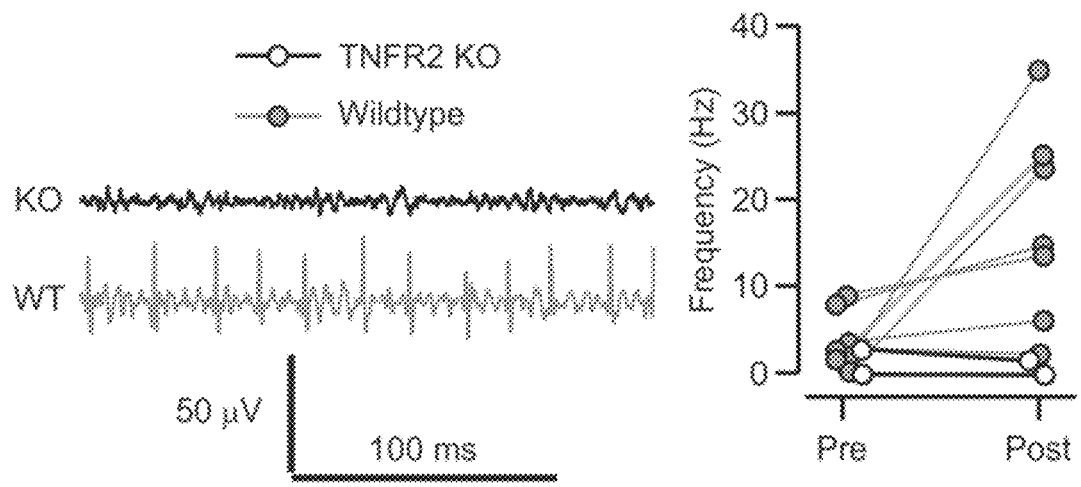
Figure 5B:
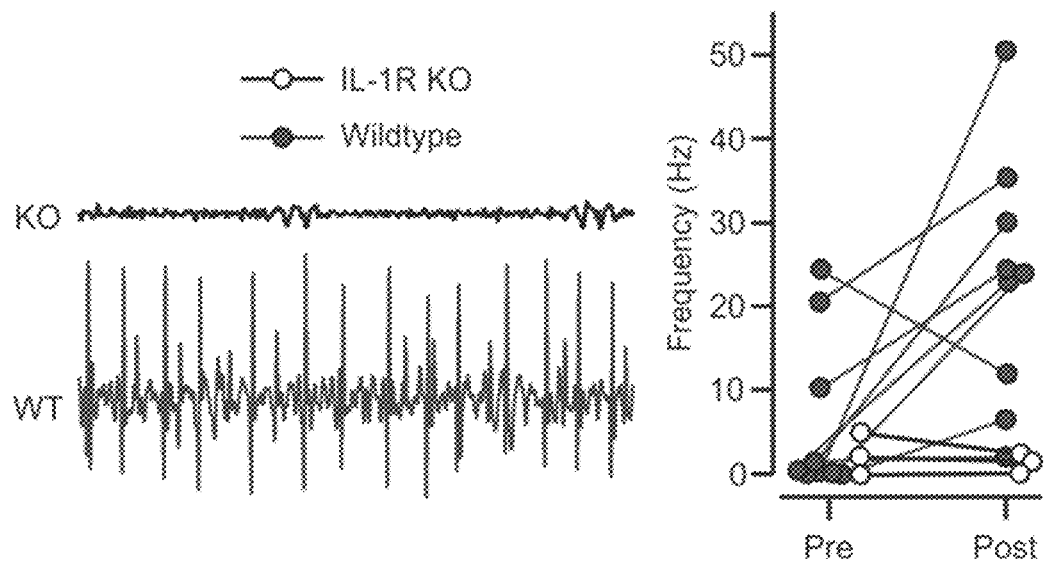

FIG. 5A-5B. Ablation of cytokine-mediated neurograms in TNFR2 and IL-1R deficient mice. (A) Left, representative traces 5 min after the application of TNF (dose of 50 µg) in TNFR2 KO and WT mice. Right, plot showing individual CAP frequencies immediately prior and after TNF (10-min intervals) in TNFR2 KO (N=3) and WT animals (N=6) (B) Left, representative traces 150 sec after the application of IL-1β (dose of 350 ng) in IL-1R KO and WT mice. Right, plot showing individual CAP frequencies immediately prior and after IL-1β (5-min intervals) in IL-1R KO (N=3) and WT animals (N=8).

Figures 6A, 6B:
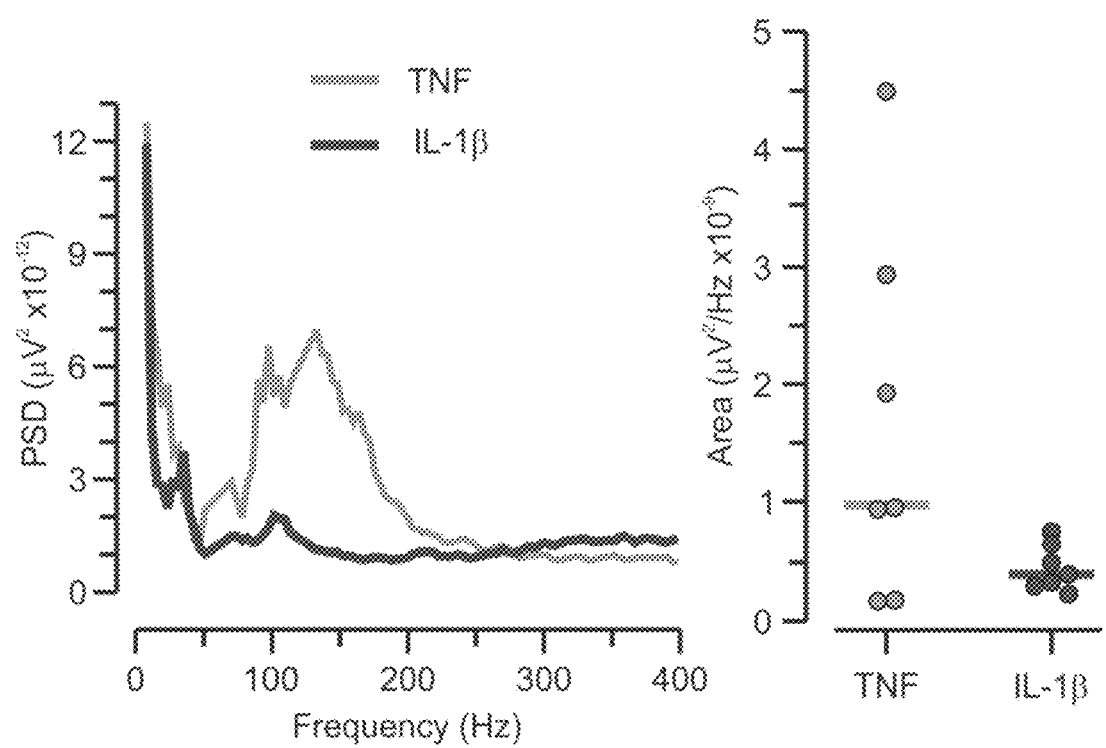

FIG. 6A-6B. Spectral analysis of TNF and IL-1β mediated neurograms. (A) Representative power spectral densities (PSD) for the TNF and IL-1β responses in the unfiltered neurogram recordings. (B) The areas under the PSDs (20-400 Hz range) were calculated for TNF and IL-1β. The calculated area for each response is shown for TNF and IL-1β, along with group averages (lines). Responses are statistically different (N=7 for each group; P=0.05, D=0.71, Kolmogorov-Smirnov test), suggesting a potential biological substrate for cytokine discrimination within the CNS.

Figure 7:
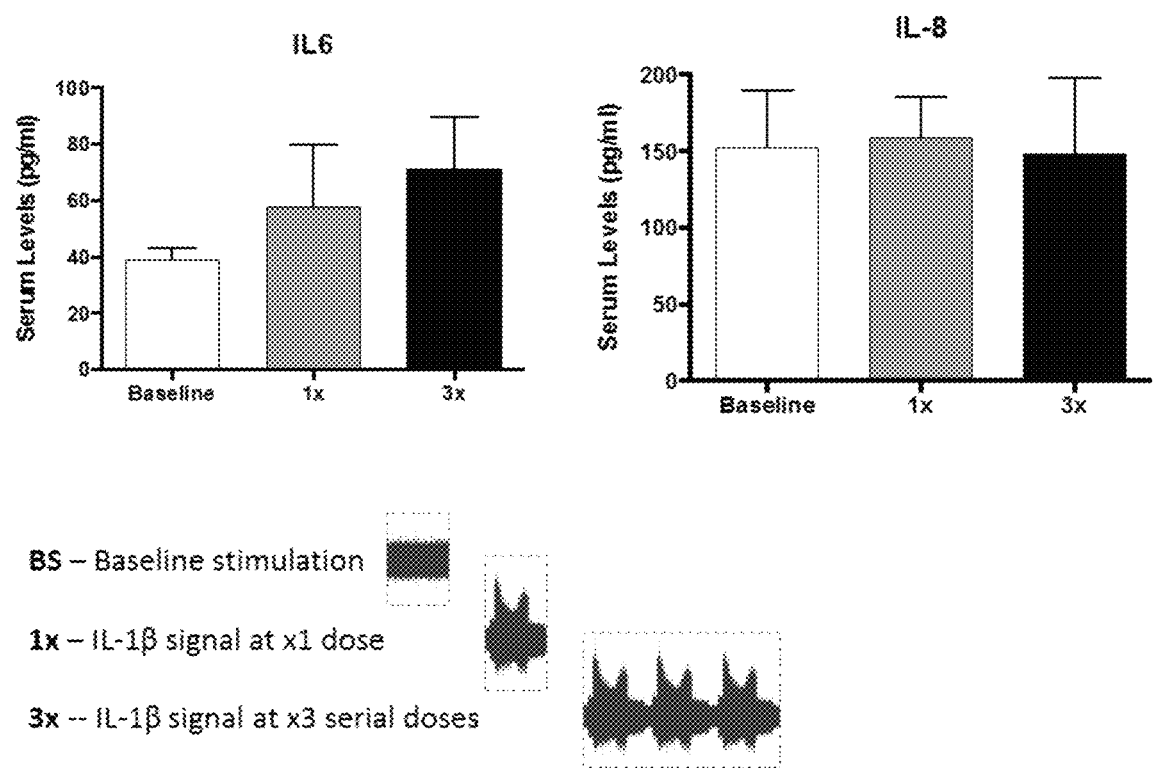

FIG. 7. Stimulating the vagus nerve of a naïve mouse with interleukin-1 beta (IL-1β)-specific neural code recapitulates IL1-induced inflammatory phenotype. Baseline or IL-1 specific signal was recorded from a mouse pre- and post-IL1 administration. The signals were converted to .wav file and re-input on the cervical vagus of a naïve mouse using an analog stimulus isolator. Serum levels of cytokines interleukin-6 (IL-6) and interleukin-8 (IL-8) were measured after 1 hr in the second mouse. The IL-1-specific signal but not the baseline signal induces increase in serum proinflammatory cytokine, IL6, levels.

Figure 8:
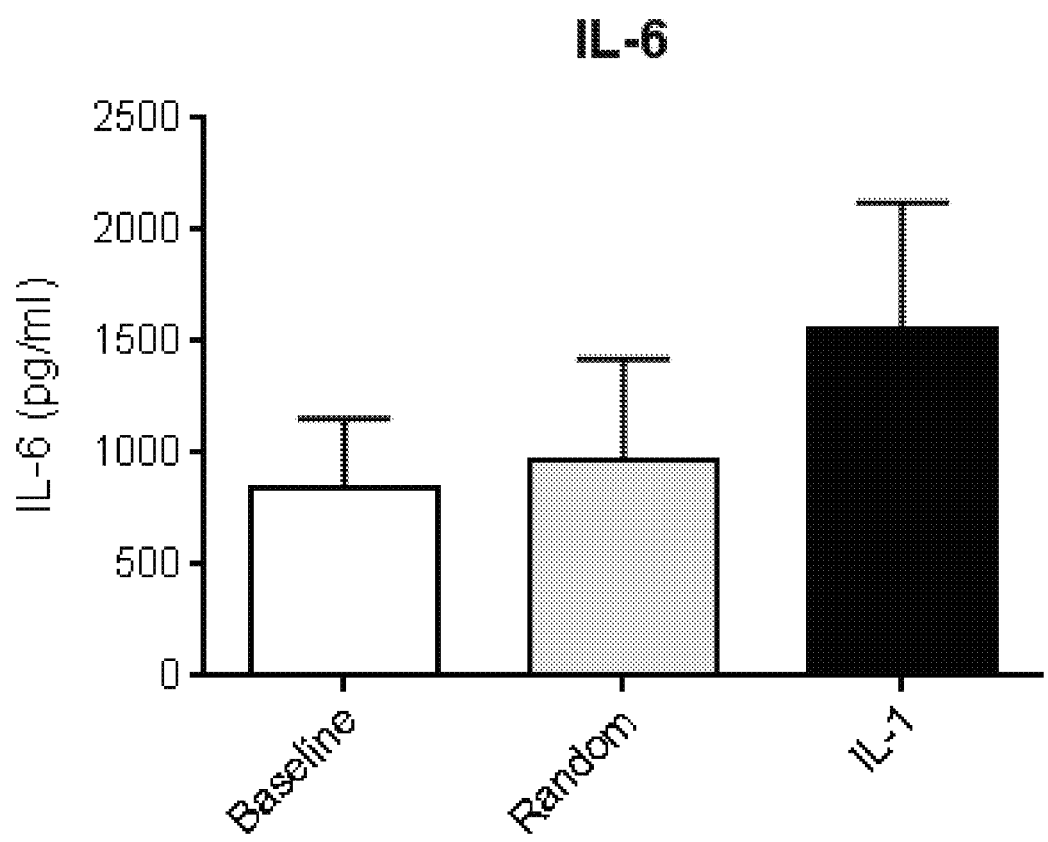

FIG. 8. Stimulating the vagus nerve of a naïve mouse with a scrambled interleukin-1 beta (IL-1β) control stimulus pattern has no effect on measured serum cytokine levels. As a control, the IL-1β-specific signal was transformed to a scrambled signal using a Matlab code that generates a randomized signal with the same amplitudes, but random frequencies maintaining the total power of the signal. Naïve receiver mice received either the baseline signal or the scrambled signal or IL-1β signal using an analog stimulator isolator. Stimulating the vagus nerve of the naïve mouse with either a baseline or a random interleukin-1 beta (IL-1β) control stimulus pattern had no effect on measured serum cytokine levels. In contrast, IL-1β-specific signal induced increased serum IL-6 levels in naïve receiver mice. Data are represented as means+S.D.; n=4 per group.

Figure 9:
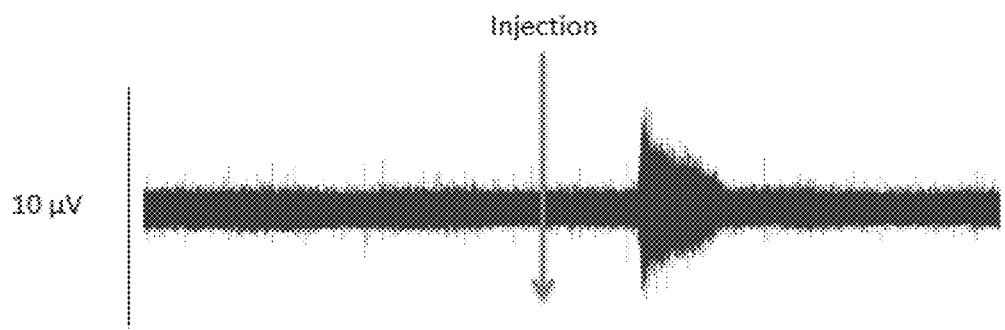

FIG. 9. Neurogram specific for anti-inflammatory cytokine IL-10 recorded from the cervical vagus nerve of a mouse. Naïve mice received a bolus of IL-10 (1 µg/mouse), and vagus nerve activity was recorded over time.

Figure 10:
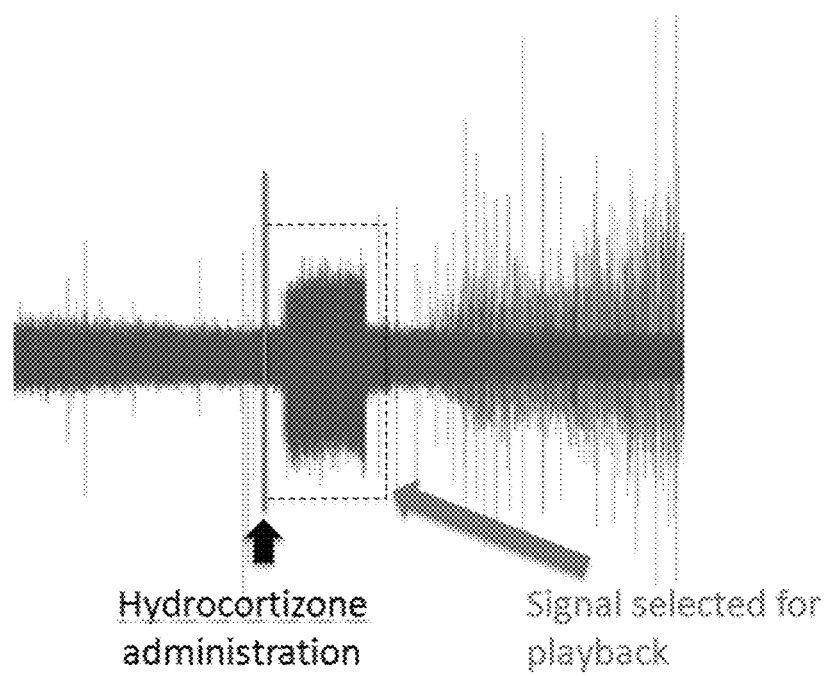

FIG. 10. Recording of hydrocortisone-induced neurogram from the cervical vagus nerve of a mouse. Naïve mice received a bolus of hydrocortisone (cortisol) (10 mg/mouse) at time point indicated as "Injection," and vagus nerve activity was recorded over time.

Figure 11:
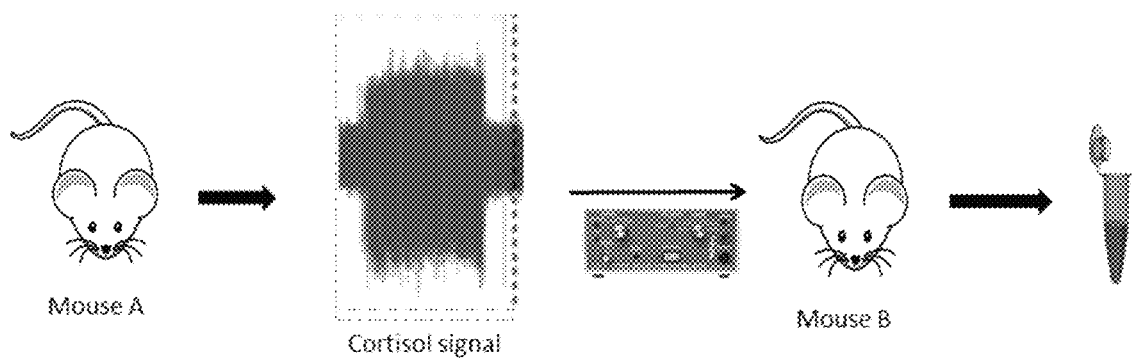

FIG. 11. Paradigm used to induce an anti-inflammatory response phenotype in naïve mice by transferring cortisol-specific vagus nerve signal. A cortisol-specific signal segment was extracted from the neurogram obtained from mouse A. The cortisol-specific signal segment from mouse A was either used as recorded or transformed to a scrambled signal using a Matlab code that generates a randomized signal with the same amplitudes, but random frequencies maintaining the total power of the signal. By dissection, the cervical vagus nerve was isolated in naïve receiver mouse B and placed on stimulating electrodes. Cortisol-specific or scrambled signal segments were transferred to receiver mouse B using an analog stimulator isolator. Blood glucose levels and serum IL-10 levels were monitored in mouse B at regular time intervals.

Figure 12:
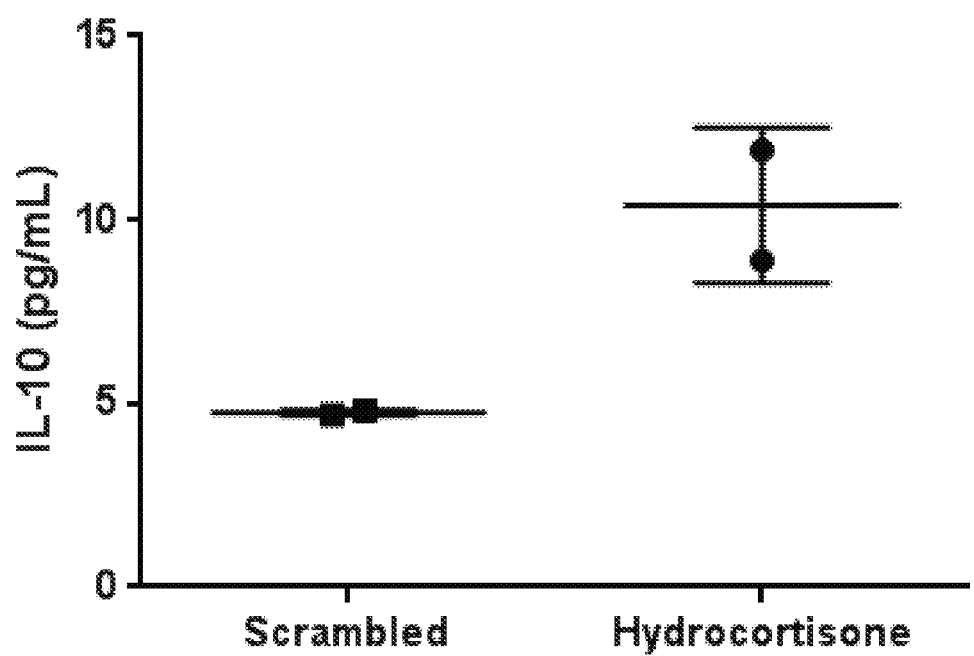

FIG. 12. Playback of cortisol-specific neurogram by direct vagus nerve stimulation induced increased levels of serum IL-10. Naïve receiver mice received either scrambled or cortisol-specific neurogram signal by direct electrical activation of the cervical vagus nerve. Serum cytokine levels were determined after 30 min. Cortisol-specific signal but not the scrambled signal induced an increase in serum levels of the anti-inflammatory cytokine IL-10.

Figure 13:
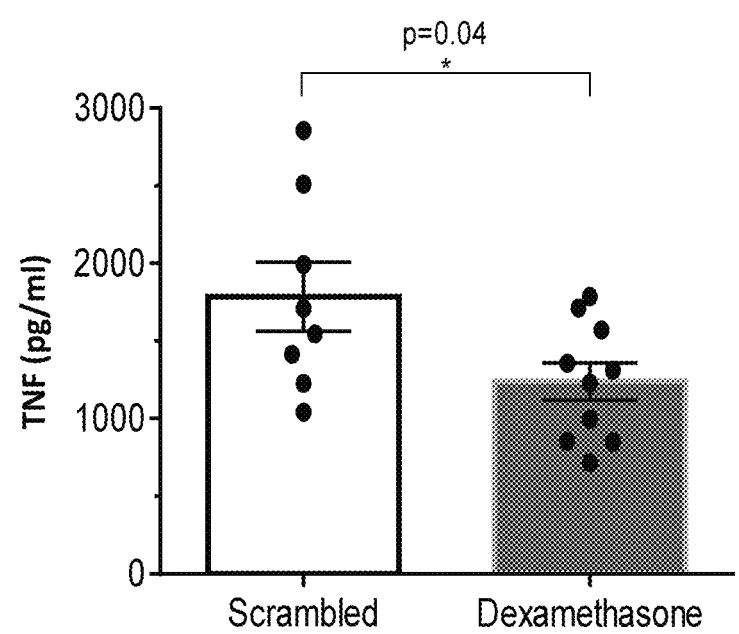

FIG. 13. Playback of dexamethasone (Dex)-specific neurogram attenuated an endotoxin-induced inflammatory response. Naïve receiver mice received either a dexamethasone (dex)-specific signal or a scrambled dex signal by direct electrical activation of the cervical vagus nerve. Animals were challenged with 0.1 mg/kg endotoxin 24 hrs post-stimulation. TNF levels were analyzed in receiver mice after 90 min. Simulation of the cervical vagus nerve with the dexamethasone-specific signal attenuated the TNF response.

Figure 14:
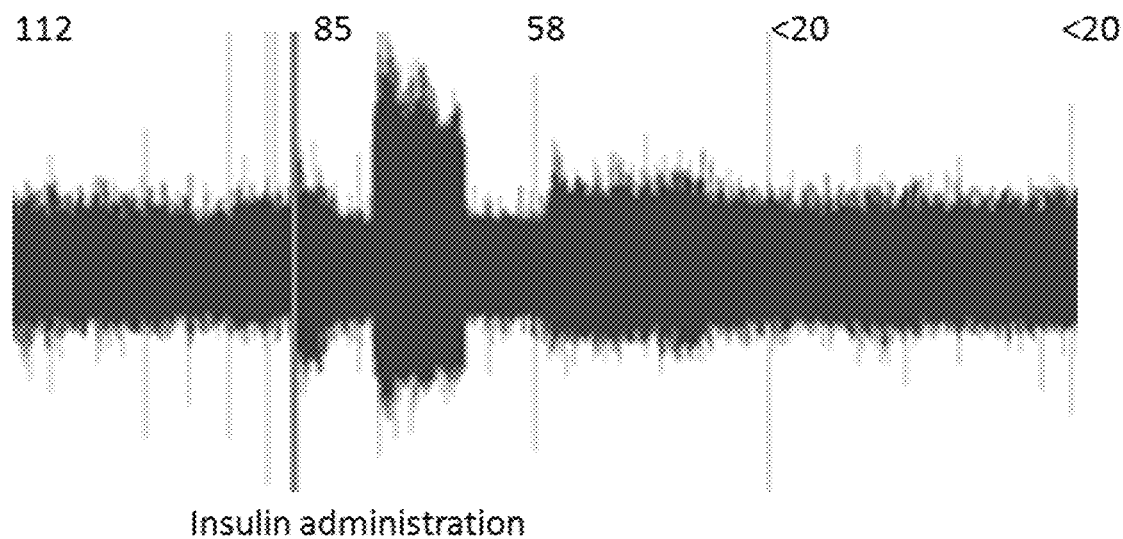

FIG. 14. Recording of hypoglycemic neurogram from the vagus nerve. Naïve mice received a bolus of insulin (6 mg/kg), and vagus nerve activity was recorded over time. The blood glucose levels were monitored every 2.5 min. Insulin induced a hypoglycemic condition in mice, as illustrated by the top line of the figure, which indicates blood glucose levels in mg/dL.

Figure 15:
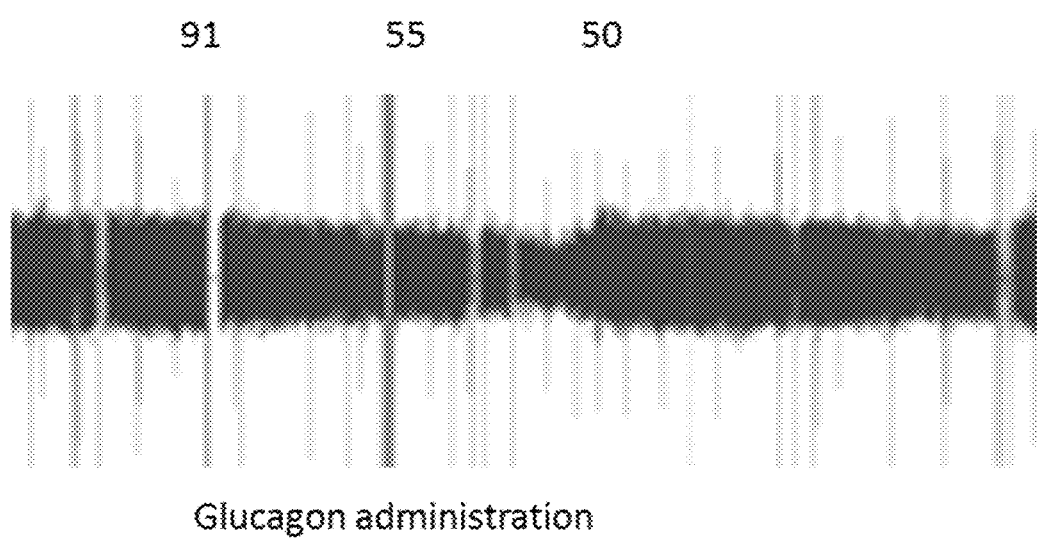

FIG. 15. Recording of euglycemic neurogram from the vagus nerve. Naïve mice received a bolus of glucagon (1 mg/kg), and vagus nerve activity was recorded over time. The blood glucose levels were monitored after every 2.5 min. Blood glucose levels are indicated in the top line of the figure in mg/dL.

Figure 16:
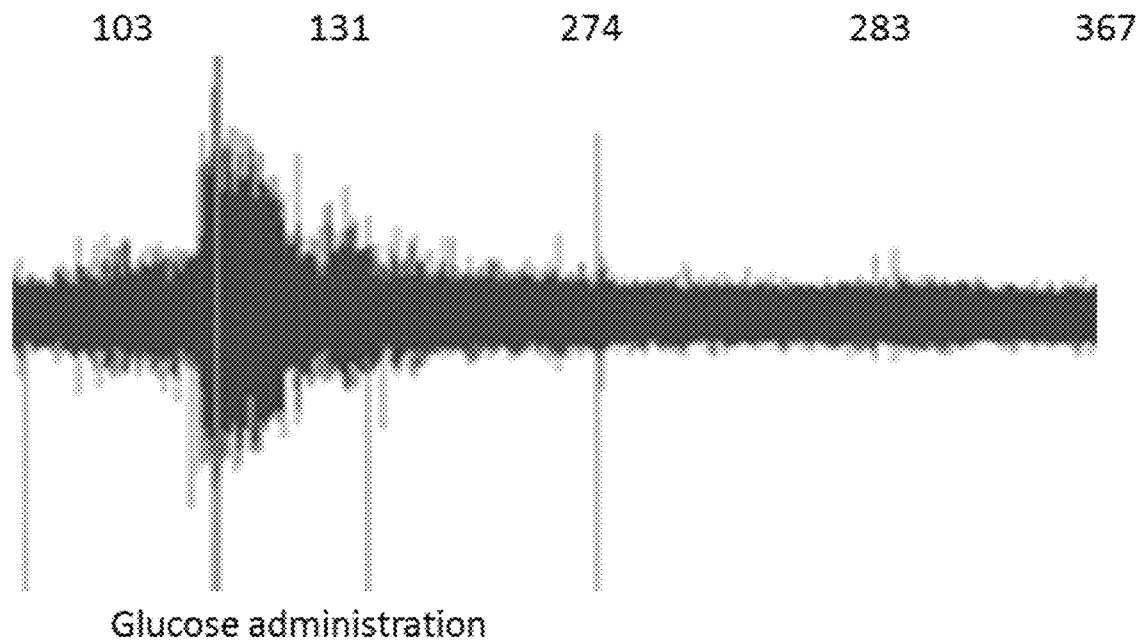

FIG. 16. Recording of hyperglycemic neurogram from the vagus nerve. Naïve mice received a bolus of glucose, and vagus nerve activity was recorded over time. The blood glucose levels were monitored after every 2.5 min. Blood glucose levels are indicated in the top line of the figure in mg/dL.

Figure 17:
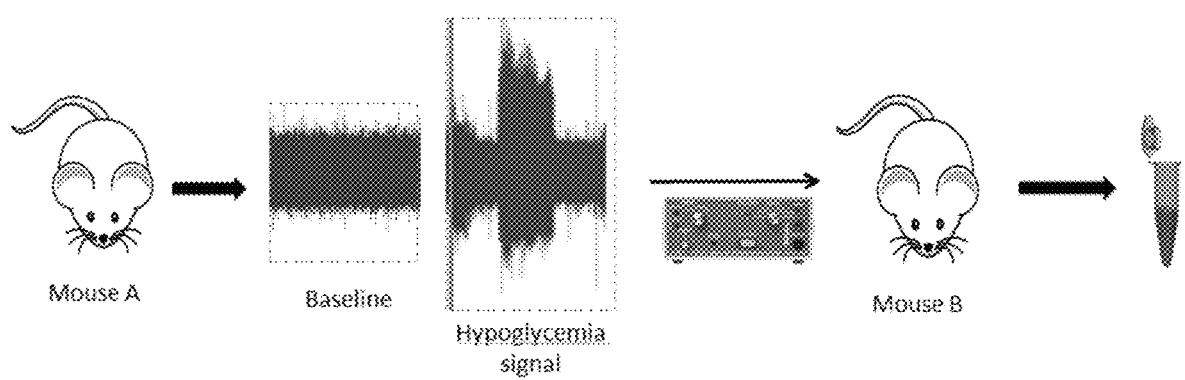

FIG. 17. Paradigm to induce a hypoglycemic phenotype in naïve mice by transferring a hypoglycemia-specific signal. Baseline or hypoglycemia-specific signal was extracted from neurograms obtained from mouse A. The cervical vagus nerve was isolated by dissection in another naïve receiver mouse B and placed on stimulating electrodes. The baseline or hypoglycemia-specific signal from mouse A was transferred using an analog stimulator isolator to the cervical vagus nerve of receiver mouse B. Blood glucose levels were monitored in mouse B at regular time intervals.

Figure 18:
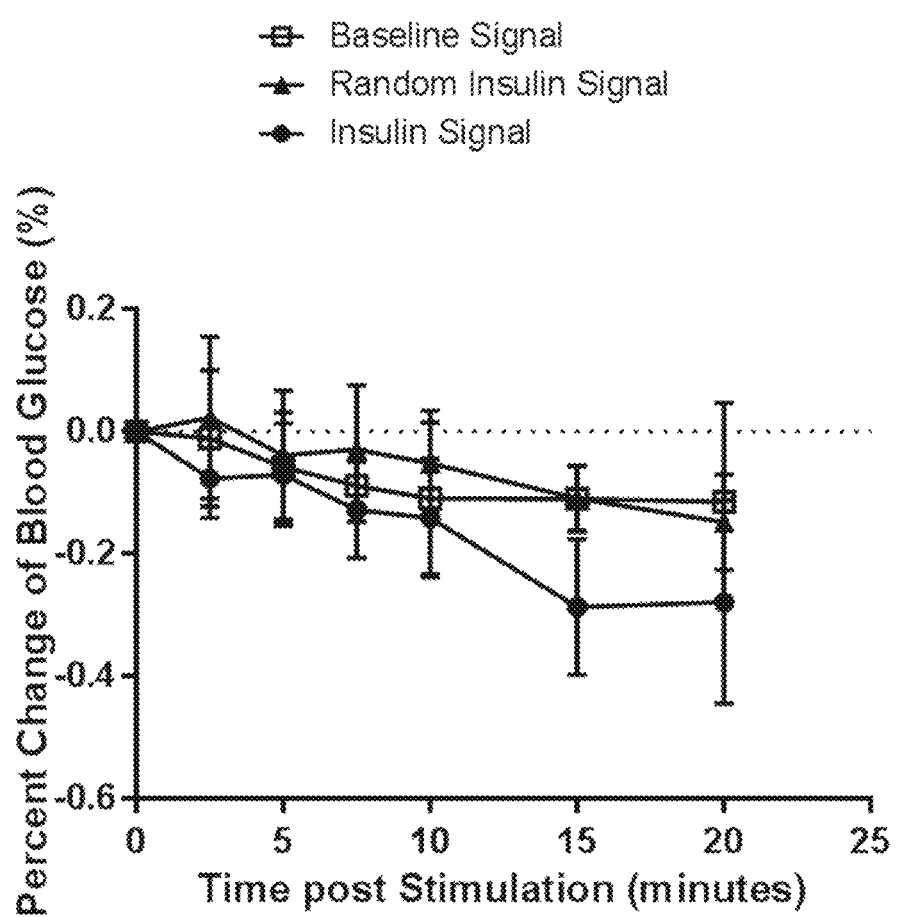

FIG. 18. Direct electric playback of a hypoglycemia, insulin-specific neurogram induced hypoglycemia in mice. Vagus nerve neurograms were recorded from mouse A (FIG. 17) receiving a bolus of insulin. A random insulin signal was generated using a Matlab code to transform an insulin signal into a randomized signal with the same amplitudes, but random frequencies maintaining the total power of the signal. The baseline, random or hypoglycemia, insulin-specific neurogram was then transferred to a naïve receiver mouse by electrical stimulation of the cervical vagus nerve. The blood glucose levels were monitored in the receiver mice over time (n=3/group).

Figure 19:
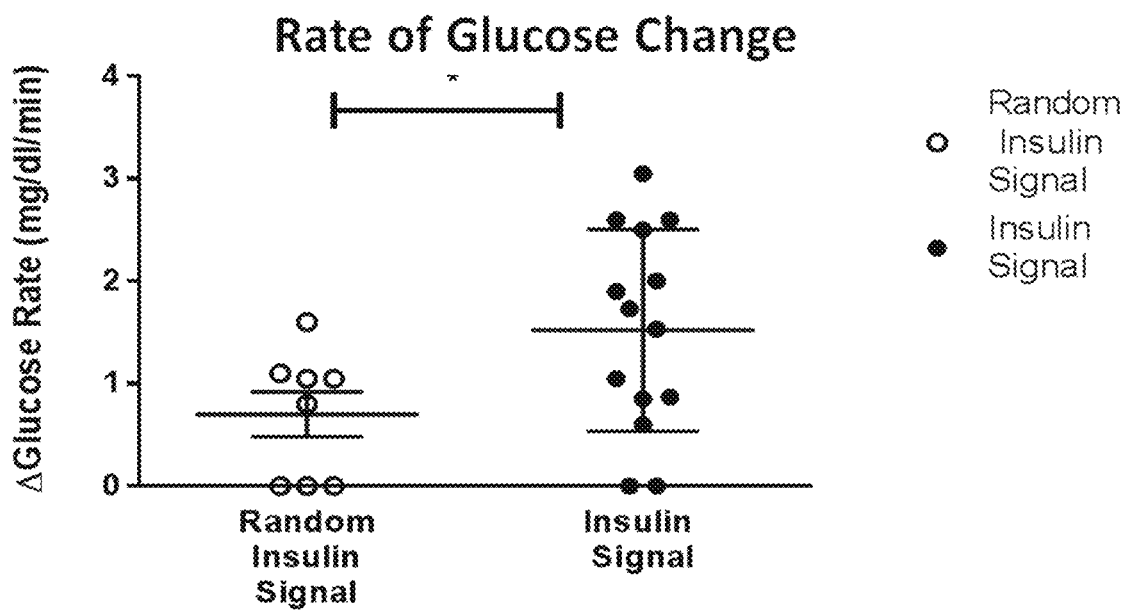

FIG. 19. Stimulating the vagus nerve of naïve mouse with an insulin stimulus pattern induced decreases in blood glucose levels. As a control, the insulin-specific signal was transformed to a scrambled signal using a Matlab code that generates a randomized signal with the same amplitudes, but random frequencies maintaining the total power of the signal. Naïve receiver mice received either the random signal or insulin signal using an analog stimulator isolator. Blood glucose was measured pre- and 20 minutes post stimulation. Stimulating the vagus nerve of the naïve mouse with a random insulin control stimulus pattern had no effect on blood glucose levels. In contrast, the insulin-specific signal induced decreases in blood glucose levels in naïve receiver mice (i.e., a larger rate of negative change in glucose levels). The data are presented as rates of change in blood glucose levels.

Figure 20:
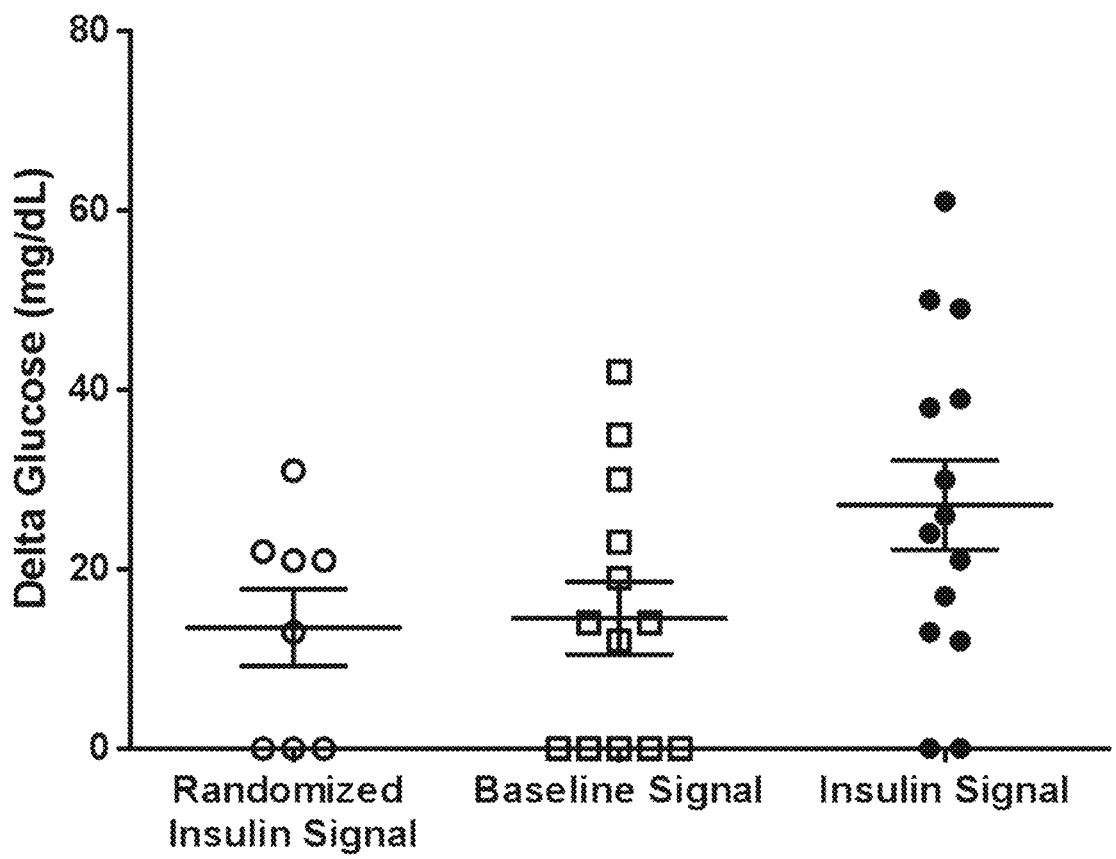

FIG. 20. Stimulating the vagus nerve of naïve mouse with an insulin stimulus pattern induced a decrease in blood glucose levels. As a control, the insulin-specific signal was transformed to a scrambled signal using a Matlab code that generates a randomized signal with the same amplitudes, but random frequencies maintaining the total power of the signal. Naïve receiver mice received either the insulin signal or random signal or a baseline signal using an analog stimulator isolator. Blood glucose was measured pre- and 20 minutes post-stimulation. Stimulating the vagus nerve of the naïve mouse with a random insulin control stimulus pattern or with a baseline signal had no effect on blood glucose levels. In contrast, the insulin-specific signal induced a decrease in blood glucose levels in naïve receiver mice (i.e., a larger negative change in glucose levels). The data are presented as changes in blood glucose levels.

Figure 21:
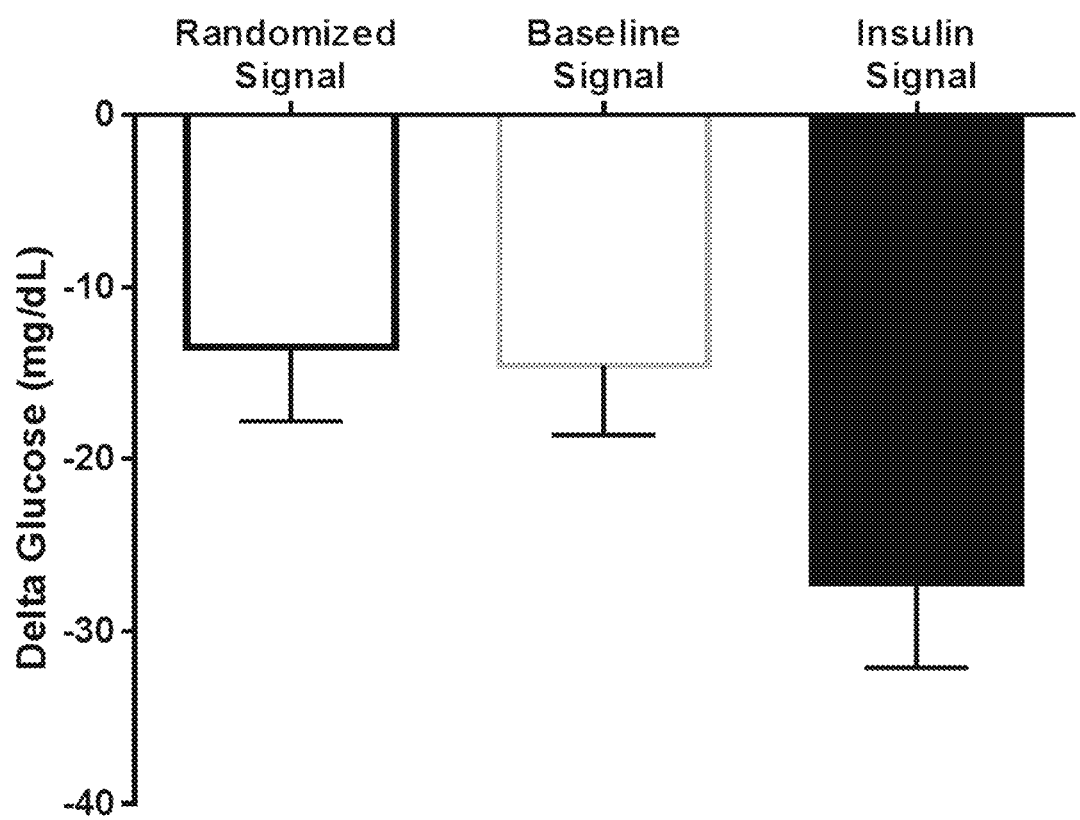

FIG. 21. Stimulating the vagus nerve of naïve mouse with an insulin stimulus pattern induced a decrease in blood glucose levels. Electrical stimulation of the vagus nerve results in lower circulating blood glucose levels after 20 minutes, compared to control stimulation with a randomized signal or with a baseline signal.

Figure 22A:
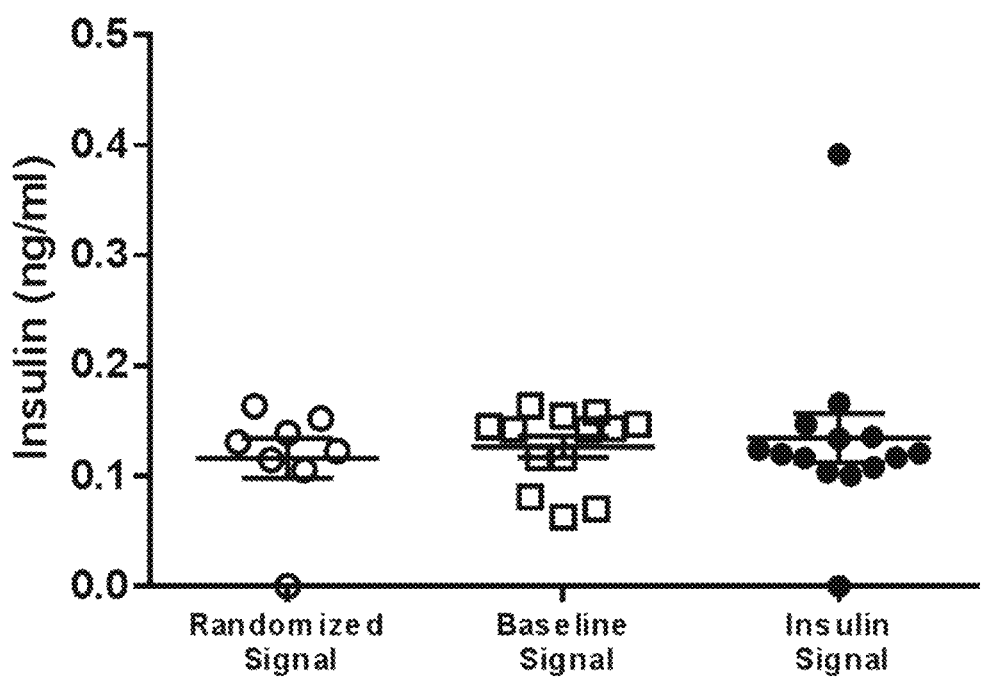
Figure 22B:
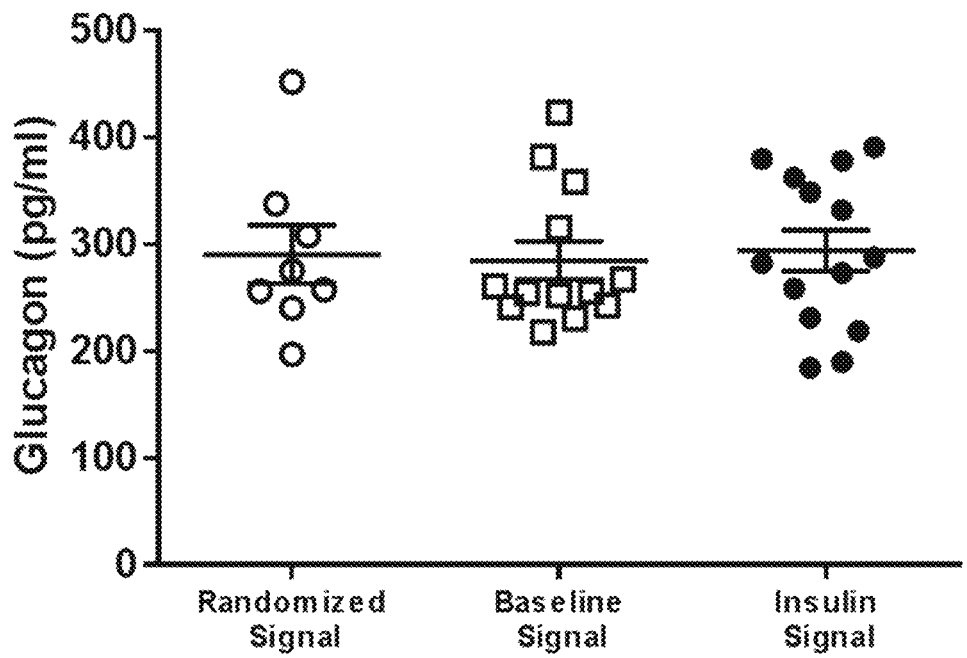
Figure 22C:
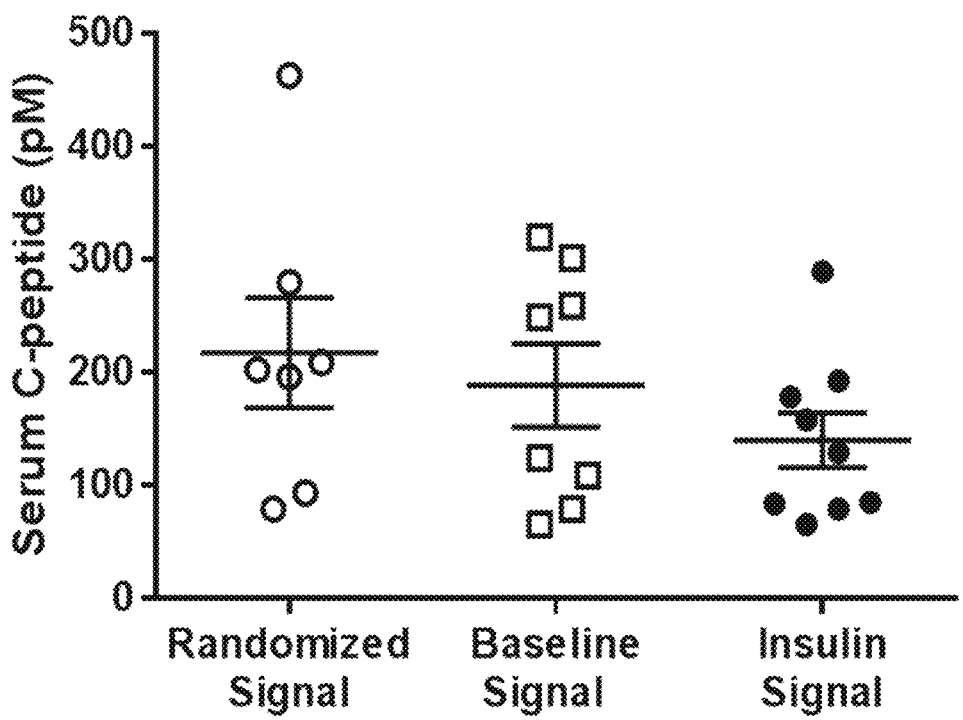

FIG. 22A-22C. The change in blood glucose levels induced by stimulating the vagus nerve with an insulin stimulus pattern is independent of insulin, glucagon and c-peptde. Vagal stimulation with an insulin stimulus pattern does not cause a significant change in circulating insulin (A), glucagon (B) or c-peptide levels (C).

Figure 23A:
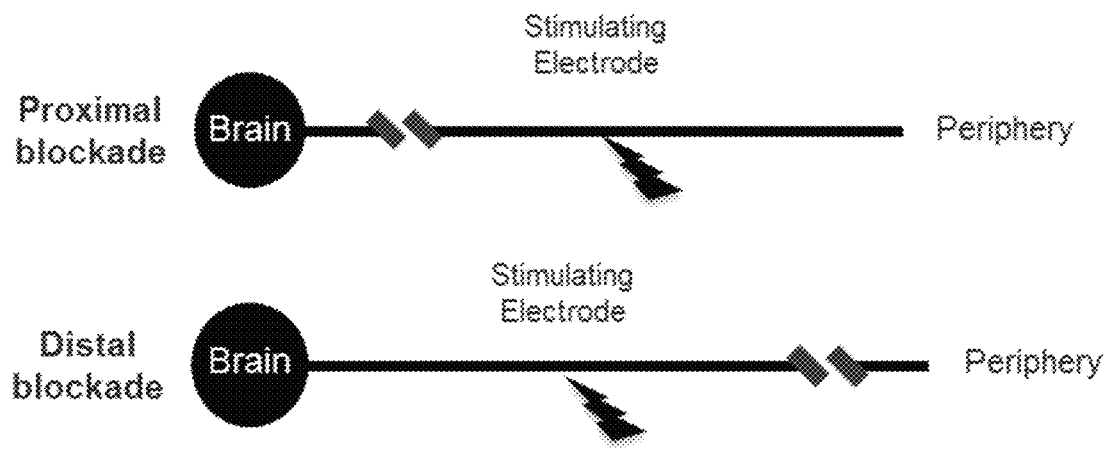
Figure 23B:
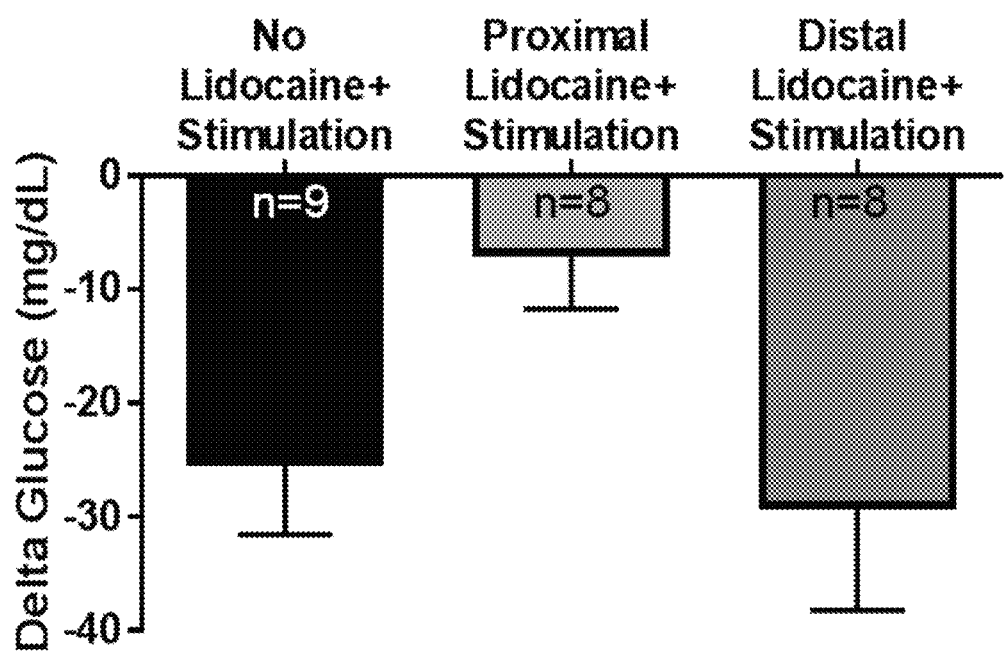
Figure 23C:
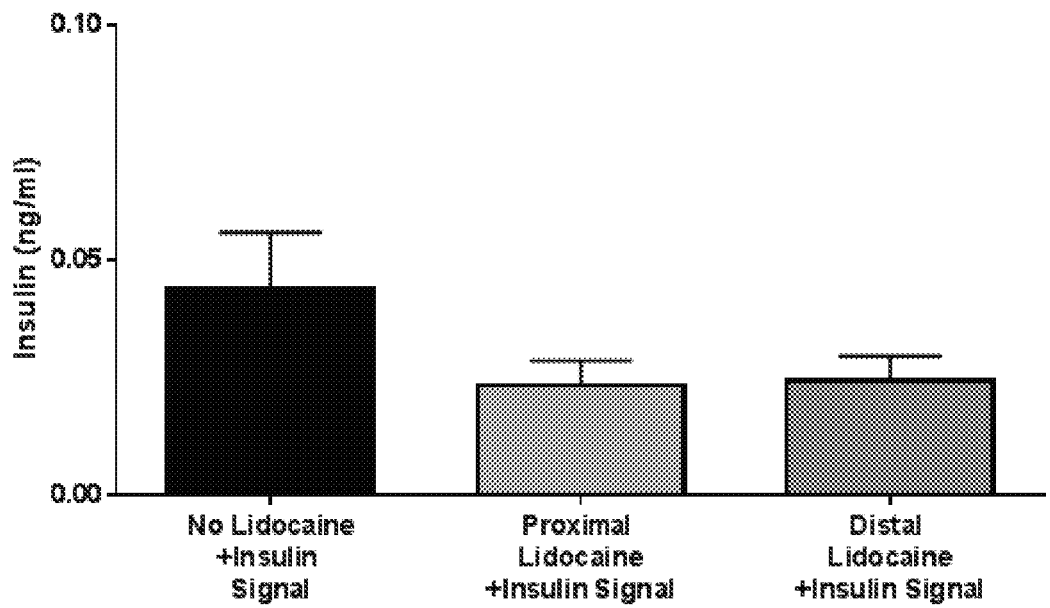
Figure 23C:
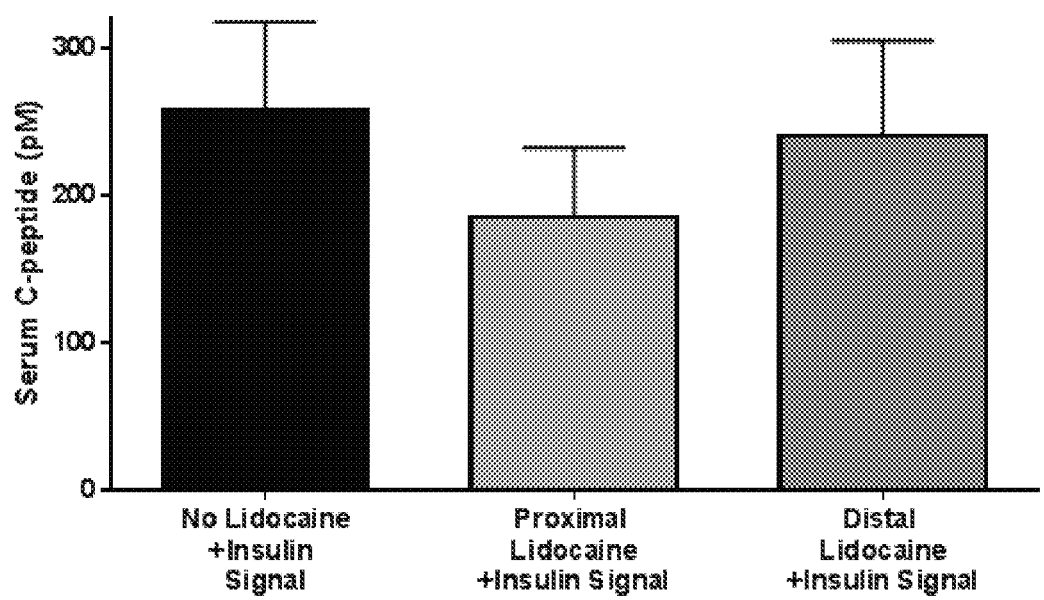

FIG. 23A-23C. Hypoglycemia induced by vagal stimulation with an insulin stimulus pattern requires afferent signaling to the brain. (A) Proximal or distal blockade of the vagus nerve with lidocaine was performed. (B) Animals with proximal vagal blockade did not respond to stimulation. In contrast, animals with distal vagal blockade did respond to stimulation. (C) Serum insulin (upper) and c-peptide (lower) levels were not significantly different.

Figure 24:
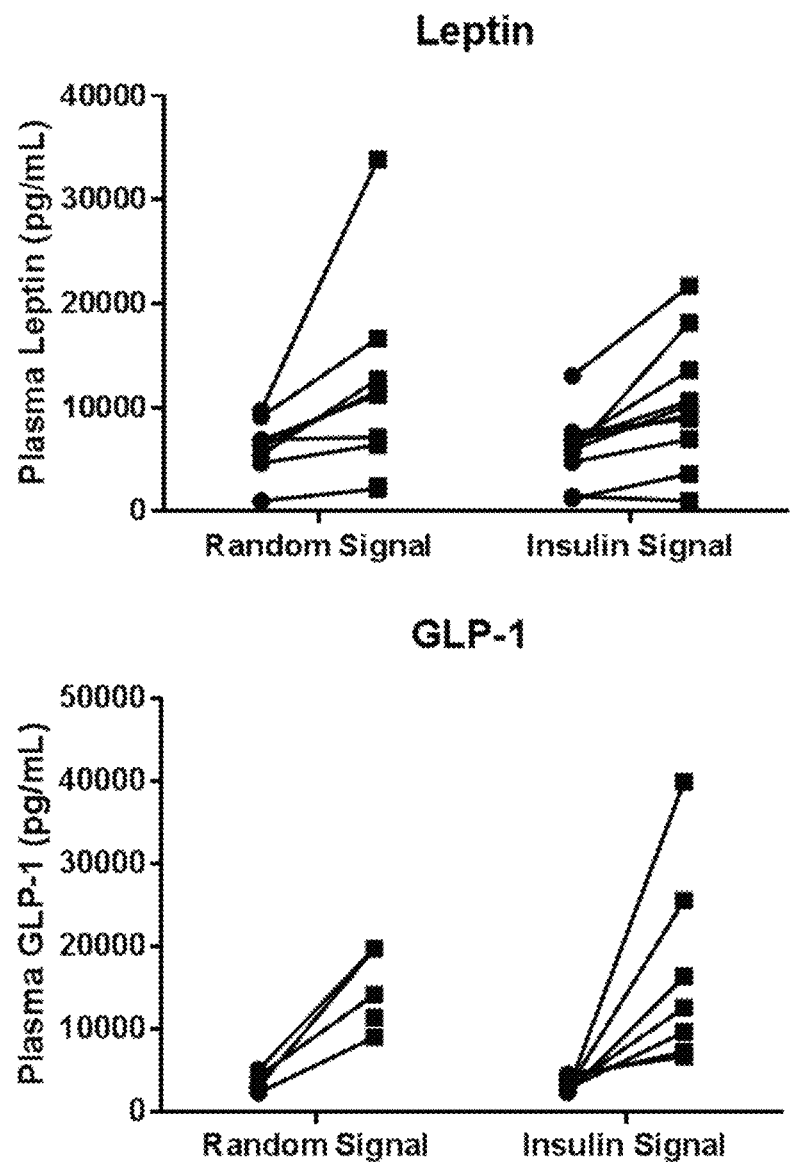

FIG. 24. Effect of vagus nerve stimulation with an insulin stimulus pattern or a random signal on levels of circulating leptin (upper) and glucagon-like peptide-1 (GLP-1) (lower).

Figure 25:
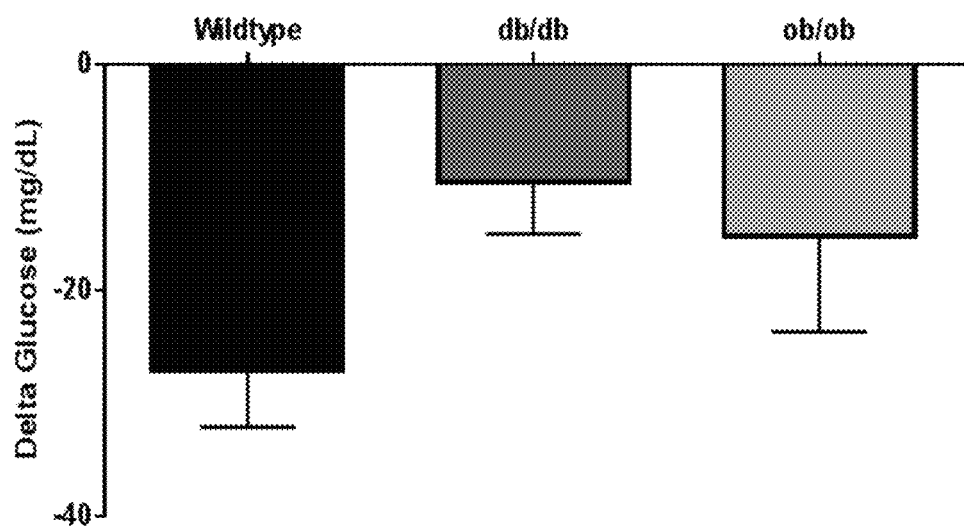

FIG. 25. The hypoglycemic effect induced by electrical stimulation of the vagus nerve with the insulin stimulus pattern requires leptin signaling, as demonstrated in leptin- and leptin receptor-knockout animals. Stimulation with insulin signal does not cause hypoglycemia in the leptin and leptin receptor knockout animals as compared to wild type.

Figure 26:
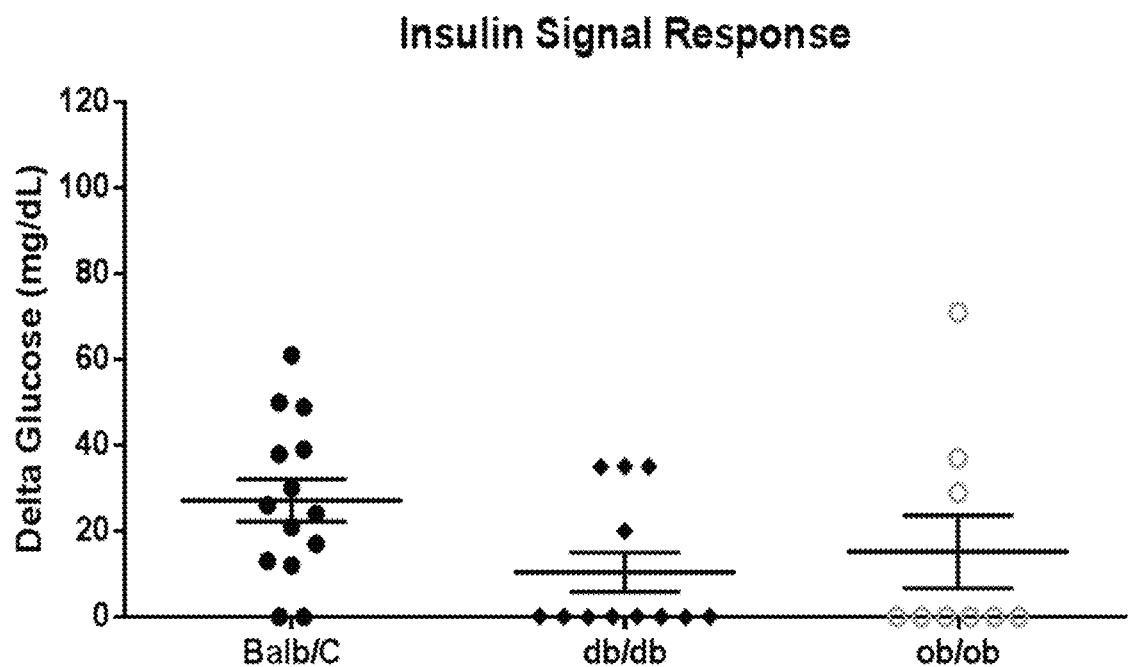

FIG. 26. Hypoglycemia response to the vagal insulin stimulus pattern requires leptin signaling. Stimulation with insulin signal does not cause hypoglycemia in the leptin and leptin receptor knockout animals as compared to wild type.

Figure 27:
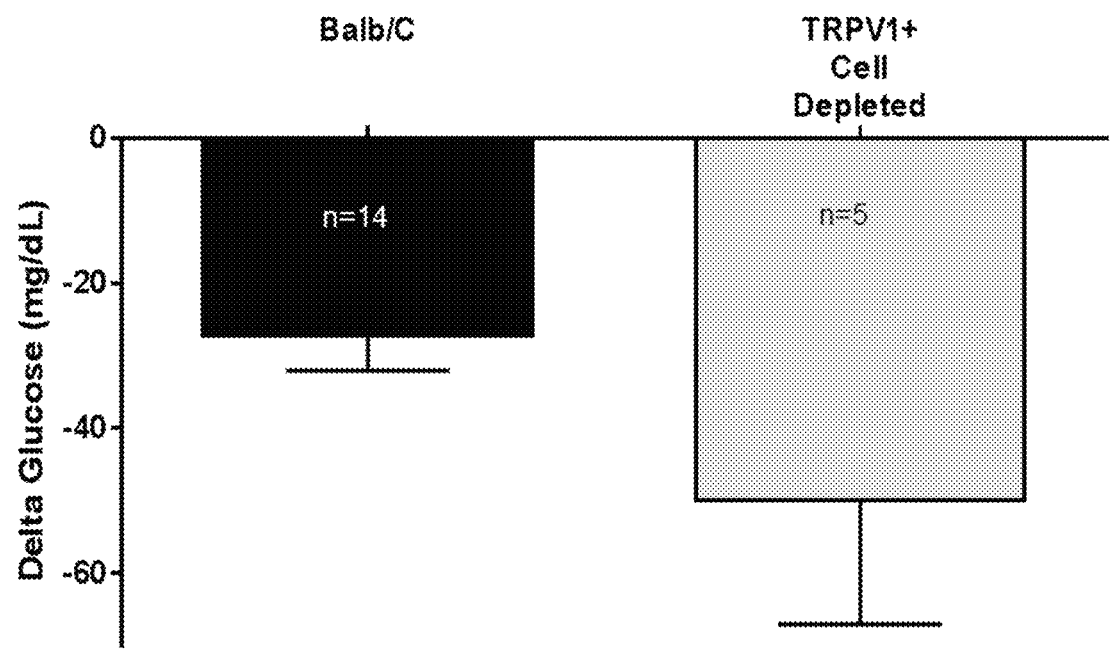

FIG. 27. Deleting transient receptor potential cation channel subfamily V member 1 (TRPV1+) neurons enhances hypoglycemia after vagus nerve stimulation. Stimulation with insulin signal induces increased hypoglycemia in animals lacking TRPV1+ neurons. These data suggest that TRPV1+ neurons may have an attenuating effect on the suppressive effect of vagus nerve stimulation.

Figure 28:
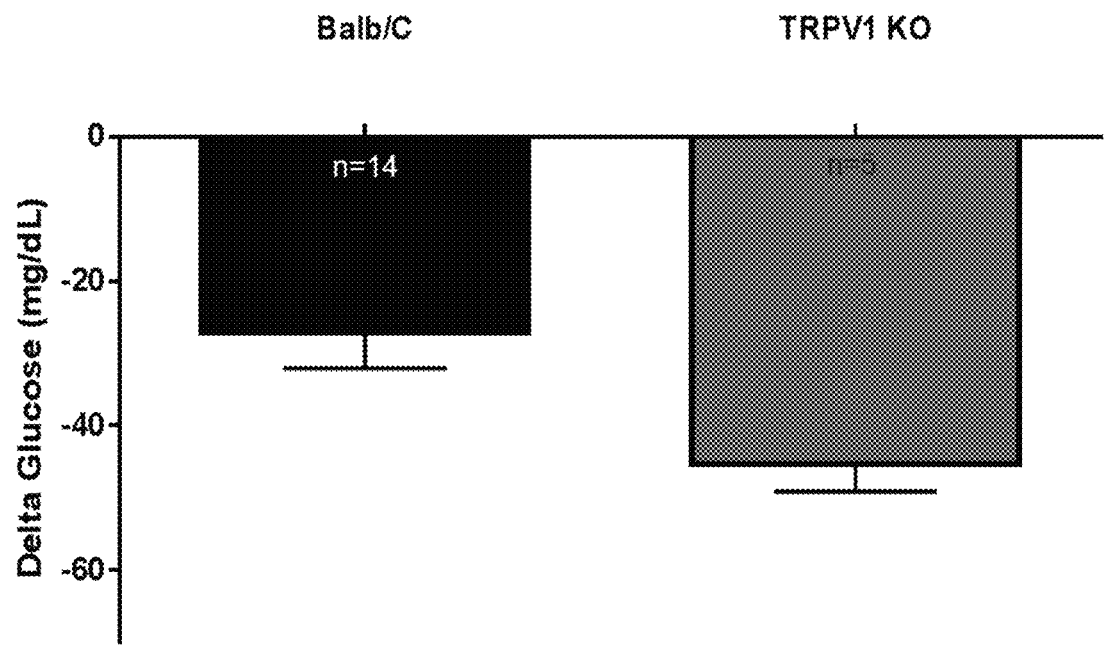

FIG. 28. Deleting TRPV1 channel expression on neurons enhances hypoglycemia after vagus nerve stimulation. Stimulation with insulin signal induces increased hypoglycemia in animals lacking TRPV1 expression. These data suggest that TRPV1+ neurons may have an attenuating effect on the suppressive effect of vagus nerve stimulation.

Figure 29:
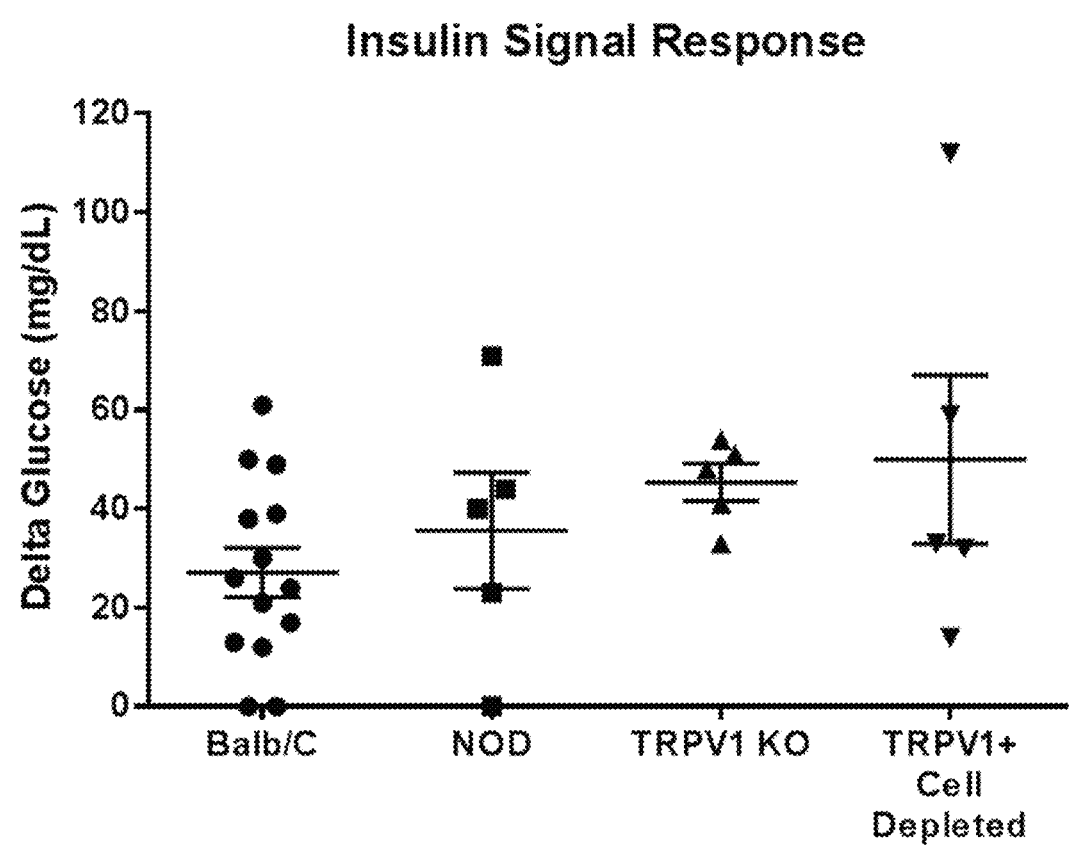

FIG. 29. TRPV1 plays an inhibitory role on circuits used to lower glucose in an insulin resistant state.

Figure 30:
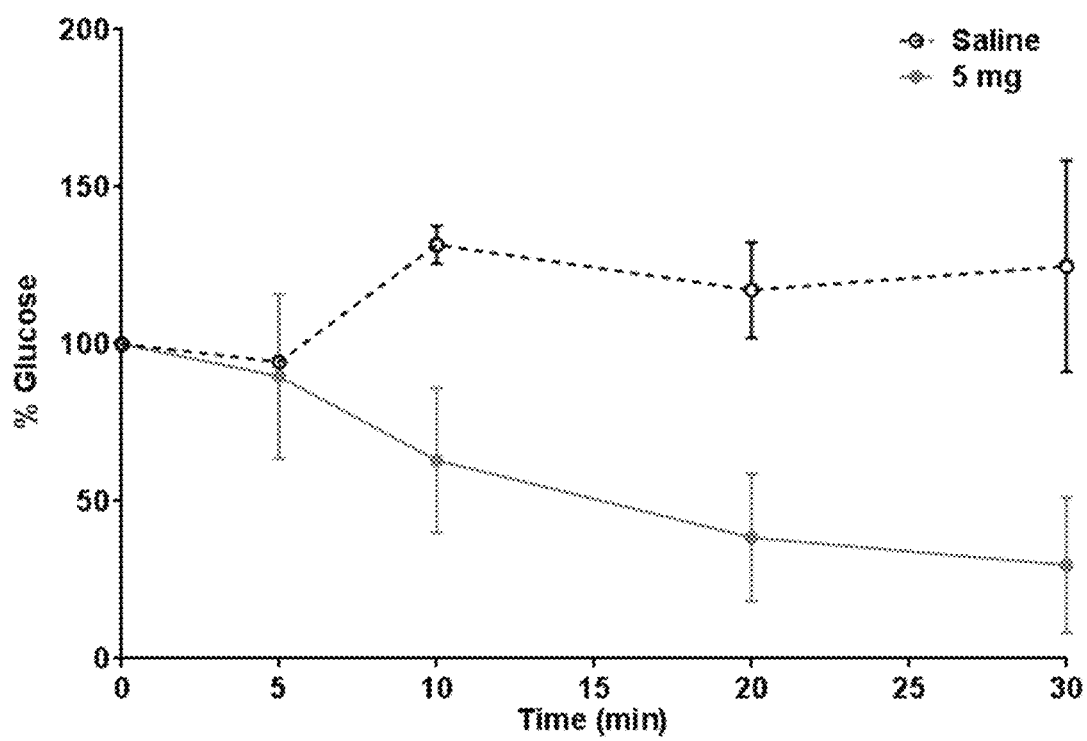

FIG. 30. Administration of cortisol-induced hypoglycemia in mice. Naïve mice received either saline or cortisol by intraperitoneal administration. Blood glucose levels were monitored over time. Cortisol but not saline administration induced hypoglycemia.

Figure 31:
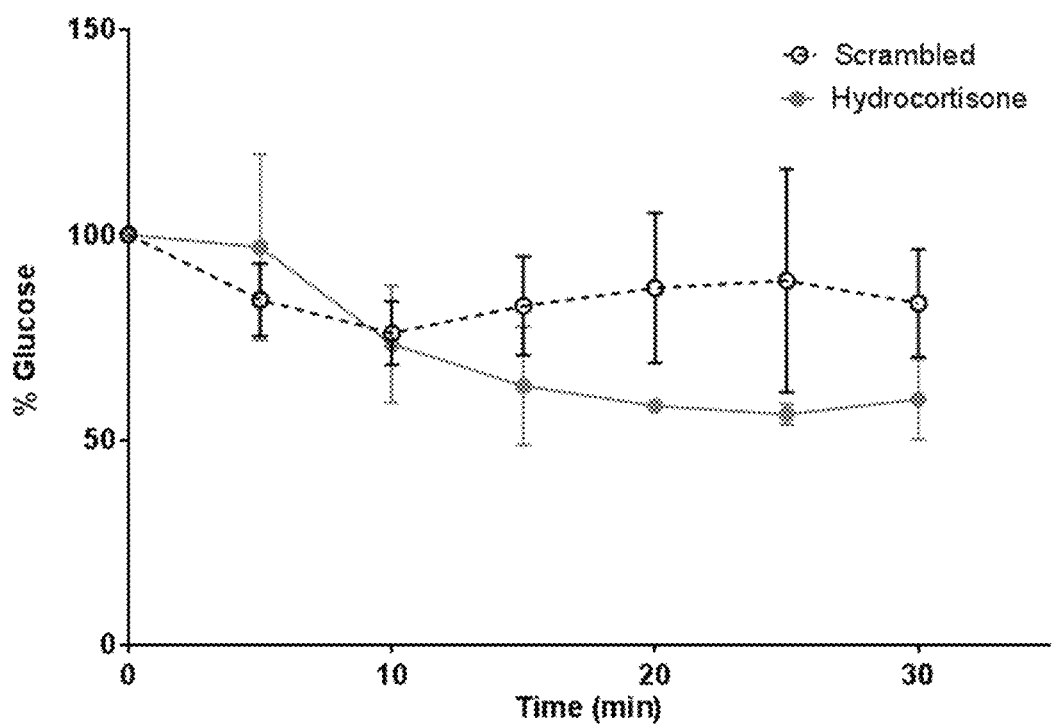

FIG. 31. Playback of cortisol-specific neurogram by direct nerve stimulation of the cervical vagus nerve induced hypoglycemia. Naïve receiver mice received either scrambled or cortisol-specific neurogram signal by direct electrical activation of the cervical vagus nerve. Blood glucose levels were monitored. The cortisol-specific signal but not the scrambled signal induced hypoglycemia.

DETAILED DESCRIPTION OF THE INVENTION

The present invention provides a method for treating a subject having a disease or disorder comprising stimulating a nerve of the subject with a corrective stimulus pattern derived from a disease-specific or condition-specific or endogenous mediator-specific or pharmacologic agent-specific neurogram in an amount and manner effective to treat the disease or disorder.

Also provided is a method for generating a corrective stimulus for the treatment of a disease or condition, comprising the steps of: providing a disease-specific, condition-specific, endogenous mediator-specific or pharmacologic agent-specific neurogram, and generating a corrective neural stimulus based therefrom.

The disease or disorder can be, for example, one or more of inflammation, type 1 diabetes, type 2 diabetes, metabolic syndrome, insulin resistance, glucose intolerance, trauma, hyperglycemia, hypoglycemia, bleeding, hemorrhagic shock, ischemia-reperfusion injury, nausea, vomiting, cancer, prostate cancer, arthritis, rheumatoid arthritis, colitis, sepsis, endotoxemia, colitis, pancreatitis, inflammatory bowel disease, Crohn's Disease, fever, anorexia, pain, swelling, kidney failure, liver disease, hypothyroidism, a host response to infection, an immune response, and a disease or disorder in which it is desirable to increase the activity or level of a cytokine.

Electrical sampling of neural activity ("neurograms") can be obtained in human or non-human subjects, such as an animal model of a disease or disorder, wherein the neurograms are disease-specific, condition-specific, endogenous mediator-specific or pharmacologic agent-specific neurograms.

The neurogram can be obtained, for example, in response to administration of physiologically occurring substances to a subject, such as for example, in response to administration of a cytokine. The cytokine can be, for example, a chemokine, a colony stimulating factor, high-mobility group protein B1 (HMGB1), an interferon (IFN), an interleukin (e.g., any of IL-1 through IL-36), a lymphokine, macrophage migration inhibitory factor (MIF), a monokine, a transforming growth factor beta (e.g., TGF-β1, TGF-β2 and TGF-β3), a tumor necrosis factor (e.g., TNFα or TNFβ). The neurogram can be obtained, for example, in response to administration of glucagon, glucose or insulin, or in response to a change in glucose levels, e.g. blood glucose levels. The neurogram can, for example, be recorded in response to a pro-inflammatory signal or an anti-inflammatory signal.

The neurogram can be obtained, for example, from a parasympathetic nerve, a sympathetic nerve, a cranial nerve, or a somatic nerve, including, for example, the vagus nerve, splenic nerve, splanchnic nerve, sciatic nerve, or a nerve to a specific organ, such as for example the spleen or liver, or portion of an organ.

The corrective stimulus pattern can be used to stimulate, for example, a parasympathetic nerve, a sympathetic nerve, a cranial nerve, or a somatic nerve, including, for example, the vagus nerve, splenic nerve, splanchnic nerve, sciatic nerve, or a nerve to a specific organ or portion of an organ. The nerve can be stimulated at different levels; for example, in the case of the vagus nerve, at the level of the cervical vagus nerve.

The present invention provides a method for controlling blood glucose levels in a subject comprising electrically stimulating a cervical vagus nerve of the subject with a corrective stimulus pattern derived from a hypoglycemic- or hyperglycemic-specific neurogram recorded from a vagus nerve in an amount and manner effective to control blood glucose levels in a subject.

In one embodiment, the method is for decreasing blood glucose levels in a subject, where the method comprises stimulating a cervical vagus nerve of the subject with a corrective stimulus pattern derived from a hypoglycemic-specific, insulin-specific or cortisol-specific neurogram recorded from a vagus nerve in an amount and manner effective to decrease blood glucose levels in a subject. The hypoglycemic-specific neurogram can be recorded from a vagus nerve of a subject following, for example, administration of insulin or cortisol to the subject. The subject receiving vagus nerve stimulation to decrease blood glucose levels can have, for example, one or more of diabetes mellitus type 1, diabetes mellitus type 2, metabolic syndrome, glucose intolerance, insulin resistance and/or hyperglycemia.

The decrease in blood glucose levels following vagal nerve stimulation can be independent of circulating levels of insulin, glucagon and c-peptide. The decrease in blood glucose levels can require leptin signaling. The decrease in blood glucose levels can be attenuated by transient receptor potential cation channel subfamily V member 1 (TRPV1). The decrease in blood glucose levels can be mediated by vagal afferent signaling.

In one embodiment, electrical stimulation of the cervical vagus nerve with a corrective stimulus pattern derived from a cortisol-specific vagal neurogram can both lower blood glucose levels and treat inflammation in the subject.

In one embodiment, the method is for increasing blood glucose levels in a treated subject, where the method comprises stimulating a cervical vagus nerve of the subject with a corrective stimulus pattern derived from a hyperglycemic-specific or glucose-specific neurogram recorded from a vagus nerve in an amount and manner effective to increase blood glucose levels in a treated subject. The hyperglycemia-specific neurogram can be recorded from a vagus nerve of a reference subject following, for example, administration of glucose to the reference subject. The treated subject receiving vagus nerve stimulation to increase blood glucose levels can have, for example, one or more of hypoglycemia, kidney failure, liver disease and/or hypothyroidism.

Also provided is a method for treating a subject having inflammation comprising electrically stimulating a cervical vagus nerve of the subject with a corrective stimulus pattern derived from an anti-inflammatory cytokine-specific or cortisol-specific or dexamethasone-specific neurogram recorded from a vagus nerve in an amount and manner effective to treat inflammation in a treated subject. The anti-inflammatory cytokine can be, for example, interleukin-4 (IL-4), interleukin-6 (IL-6), interleukin-10 (IL-10), interleukin-11 (IL-11), interleukin-13 (IL-13) or interleukin-35 (IL-35). Stimulation of the cervical vagus nerve with a corrective stimulus pattern derived from an anti-inflammatory cytokine-specific or cortisol-specific or dexamethasone-specific neurogram can increase serum levels of one or more anti-inflammatory cytokine, such as, for example, one or more of interleukin-4 (IL-4), interleukin-6 (IL-6), interleukin-10 (IL-10), interleukin-11 (IL-11), interleukin-13 (IL-13) and interleukin-35 (IL-35). Stimulation of the cervical vagus nerve with the corrective stimulus pattern derived from an anti-inflammatory cytokine-specific or cortisol-specific or dexamethasone-specific neurogram can decrease serum levels of one or more inflammatory cytokine, such as for example one or more of interleukin-1β (IL-1β) and tumor necrosis factor (TNF). The subject receiving vagus nerve stimulation to treat inflammation can have, for example, one or more of rheumatoid arthritis, colitis, inflammatory bowel disease, Crohn's Disease, and an infection, such as, for example, a bacterial infection.

Also provided is a method for treating a subject having a disease or disorder comprising stimulating a cervical vagus nerve of the subject with a corrective stimulus pattern derived from an interleukin-1β (IL-1β)- or tumor necrosis factor (TNF)-specific neurogram recorded from the vagus nerve in an amount and manner effective to treat the disease or disorder. The disease or disorder can be any disease or disorder in which it is desirable to increase the activity and/or serum levels of interleukin-1β (IL-1β) and/or tumor necrosis factor (TNF). For example, stimulation of the cervical vagus nerve of a subject with an interleukin-1 beta (IL-1β)-specific neural code can recapitulate an IL1-induced inflammatory phenotype.

In one embodiment, the corrective stimulus pattern is applied to the vagus nerve and the physiologic effects of the corrective stimulus pattern are mediated by vagal nerve afferents.

Nerve recording and/or nerve stimulation can be carried out, for example, using implantable electrodes, such as, for example, a cuff-style electrode. Preferably, vagal neurograms are obtained from a cervical vagus nerve. The neurograms can be obtained from the same subject that is being treated with nerve stimulation or from a different subject. Preferably, stimulation protocols are able to read, interpret and respond to a patient's active state of a disease or disorder. Neurograms can be obtained from an animal model or a human patient. The subject being treated can be a human subject or a veterinary subject.

Also provided, for example, is the use of a corrective stimulus pattern derived from a disease-specific or condition-specific or endogenous mediator-specific or pharmacologic agent-specific vagus nerve neurogram for treating a subject having inflammation, hypoglycemia or hyperglycemia by a method comprising electrically stimulating a cervical vagus nerve of the subject in an amount and manner effective to treat inflammation, hypoglycemia or hyperglycemia.

This invention will be better understood from the Experimental Details, which follow. However, one skilled in the art will readily appreciate that the specific methods and results discussed are merely illustrative of the invention as described more fully in the claims that follow thereafter.

EXPERIMENTAL DETAILS

Example 1. Cytokine-Specific Neurograms Recorded from the Afferent Vagus Nerve

Overview

Neural networks in the periphery send signals about the body's physiological state to the central nervous system (CNS) through afferent fibers, and particularly through the vagus nerve (VN). As part of this network, the sensory vagus nerve responds to interleukin-1β (IL-1β) and lipopolysaccharide, and relays these signals to the nucleus tractus solitarius within the CNS. The present study mapped the peripheral neural activity that occurred in response to tumor necrosis factor (TNF) and IL-1β by recording from the cervical vagus nerve of adult mice. With the use of selective surgical vagotomies, the neurograms generated by cytokines were shown to be carried by the afferent fibers of the vagus nerve. Low doses of cytokines (5 μg TNF or 35 ng IL-1β) did not enhance baseline activity of the vagus nerve, whereas higher doses (50 μg TNF or 350 ng IL-1β) triggered significant enhancements. Analysis of temporal dynamics and power spectral characteristics of neurograms mediated by TNF and IL-1β revealed cytokine-selective signals in the vagus nerve.

Materials and Methods

Animals. All experimental protocols were approved by the Institutional Animal Care and Use Committee (IACUC) at The Feinstein Institute for Medical Research, Northwell Health (formerly the North Shore-LIJ Health System), which follows the NIH guidelines for ethical treatment of animals. The studies used male BALB/c mice (8-12 weeks, weighing 20-30 g), which were purchased from The Jackson Laboratory (Bar Harbor, Me.). They were housed at 25° C., with ad libitum water and chow, and acclimated to a 12-h light and dark cycle for >3 days prior to conducting experiments.

Chemicals. Lidocaine, tetrodotoxin (Sigma-Aldrich), and human IL-1β (eBiosciences) were purchased. Recombinant and tag-free human TNF was produced in-house. Following expression in *E. coli*, TNF was purified using a cation exchange column and endotoxins removed by phase separation with Triton X-114.

In vivo VN recordings. Mice were fasted (3-4 h) prior to each experiment. They were induced (isoflurane at 2.5%) and maintained (isoflurane at 1.5%) in the supine position for surgery. A midline cervical incision was made and the left cervical branch of the vagus nerve isolated from the accompanying carotid bundle. Under magnification, the connective tissue was mechanically removed, and the vagus nerve was placed over three custom-built silver hook electrodes. Electrophysiological signals were digitized (sampling rate, 32 kHz) through a data acquisition system (Digital Lynx 4SX, Cheetah v5 software, Neuralynx, Bozeman, Mont.) and referenced to an animal ground electrode placed between the skin and right salivary gland. In all experiments, the vagus nerve was protected from desiccation and insulated by bathing the surgical field in mineral oil. Following acquisition of baseline activity (15-20 min), animals were i.p. injected with TNF, IL-1β, or saline control, and recordings were continued for 20-30 min post-injection. The experimenter was grounded whenever manipulating the animal during recordings.

Figure 2A:
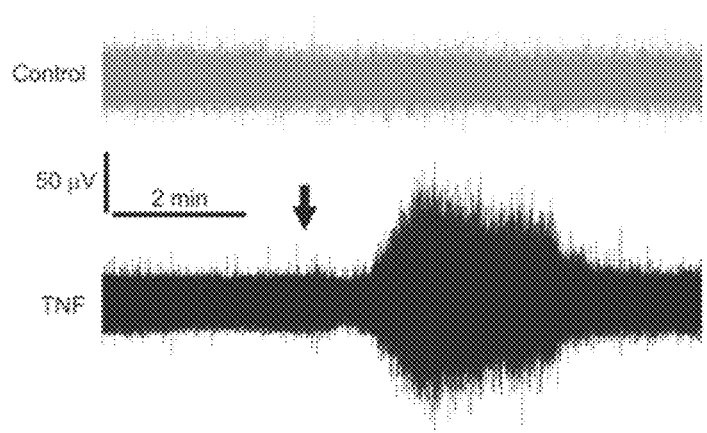
Figure 2B:
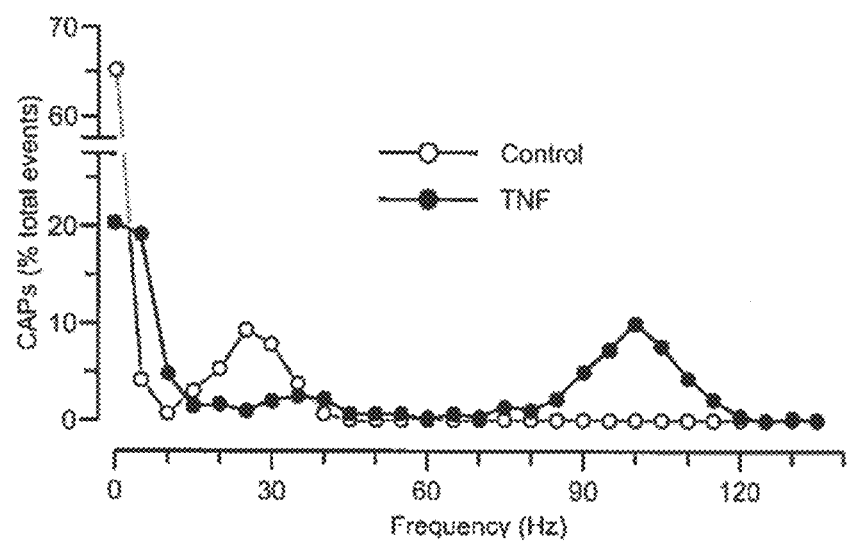
Figure 2C:
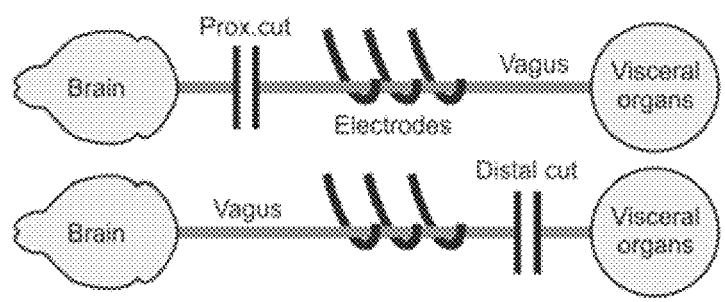
Figure 2D:
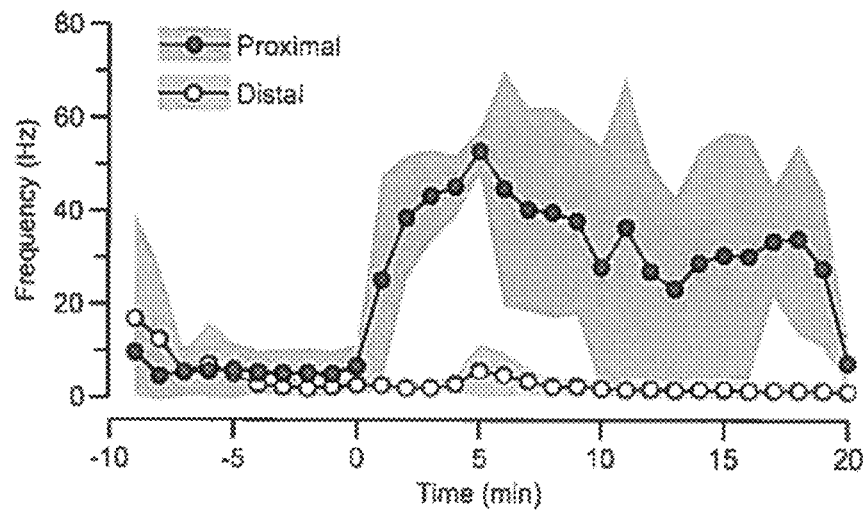
Figure 2E:
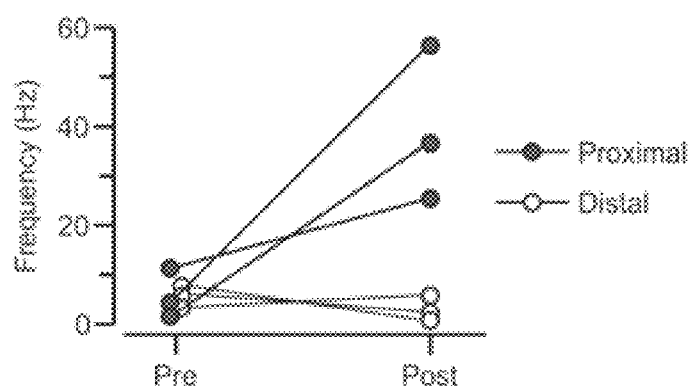

Vagotomies. A surgical transection of the vagus nerve was completed either proximal or distal to the hook electrodes, using the brain as the point of reference (FIG. 2D). Following placement of the vagus nerve on the hook electrodes, a silk suture was passed under and secured to the vagus nerve with a single knot. Ethyl cyanoacrylate was used to adhere the vagus nerve to the silk suture and the surgical transection completed.

Vagus nerve evoked responses. The vagus nerve was placed on a wet tissue paper laid over a custom acrylic platform and kept moist using artificial cerebral spinal fluid (126 mM NaCl, 26 mM NaHCO3, 10 mM glucose, 2.5 mM KCl, 2.4 mM $CaCl_2$, 1.3 mM $MgCl_2$, and 1.2 mM $NaH_2PO_4$). A recording electrode (glass pipette filled with 2M NaCl) and a stimulating electrode (FHC, Bowdoin, Me.) were placed onto the vagus nerve, with the latter 4-5 mm away from the former (and farther from the head). Signals were amplified (x1000, model 1800, AM Systems, Everett Wash.) and digitized (30 kHz) through an acquisition system (Micro1400 unit and Spike2 version 7 software, CED, Cambridge, UK). Stimuli (20-µs long) of increasing intensity (1-50 V) were delivered with a stimulator (SD9, Grass, Warwick R.I.) to generate an input/output curves (1-V increments in the 1-10 range, 5-V increments in the 10-50 range), which were generated first in a saline solution and then in the setting of either lidocaine (2%) or tetrodotoxin (100 µM). The responses were assessed by integrating the area between the response curve and the baseline value (determined 1-10 ms prior to stimulation).

Data analysis. Spike2 software (version 7, CED) was used for analysis of raw recordings, which were filtered (using high pass filter with an edge of 160 Hz) and smoothed. Neural signals were identified by user-specified adaptive threshold methodology. Identified compound action potentials (CAPs) were reviewed and signals erroneously captured by the adaptive threshold were manually removed. Also ignored were all areas of signal saturation, as well as signals corresponding to cardiac and respiratory components. Following this signal processing, information regarding rate and temporal coding patterns were extracted and further analyzed using OriginPro software (version 8, OriginLab, Northampton, Mass.). Neurograms were defined as the first interval of time in which the CAP frequency was >3x baseline level. TNF and IL-1β neurograms were extracted and subjected to Fast Fourier Transform (FFT) for PSD analysis (frequency resolution of 3.9 Hz, using a Hanning window). Within the frequency domain, notch filters were applied (60±10 and 120±10 Hz) to minimize the contribution of electrical noise along with its dominant harmonic. Data were linearly interpolated between the notch-filtered intervals. The areas under the PSDs (20-400 Hz range) were calculated for each cytokine response.

Statistical tests. Data are presented as individual samples, mean±SD, and mean±SEM. The Shapiro-Wilk test was used to test for normality. ANOVA, Student t test, Mann-Whitney U test, and Kolmogorov-Smirnov test were used to examine for statistical significance. P values <0.05 were considered significant.

Results

Figure 1B:
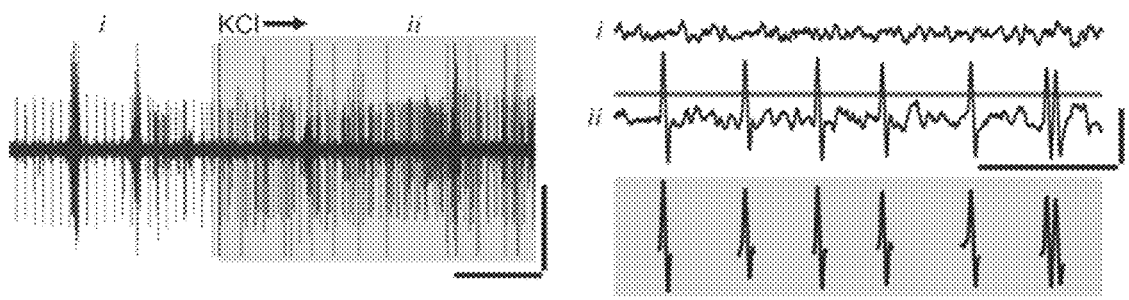
Figure 1C:
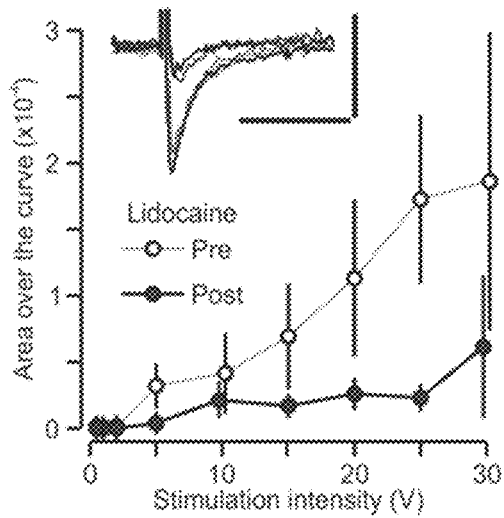
Figure 1D:
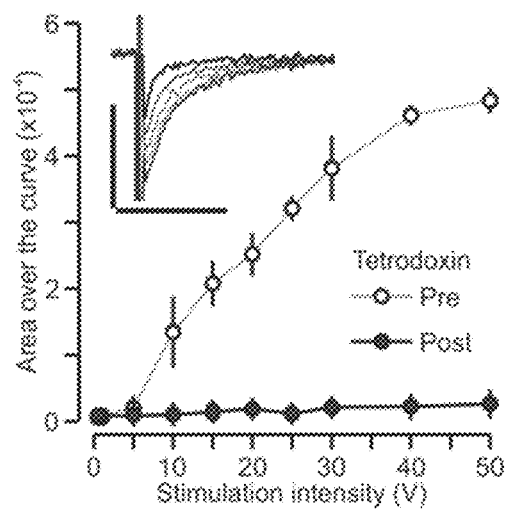

Vagus nerve (VN) recordings capture neural compound action potentials. To investigate the vagus nerve's neural activity, an electrophysiological recording system was constructed with three hook electrodes. The signals were digitized, subjected to high-pass filtering, and post-acquisition smoothing algorithms (as described in Methods). The recorded signal showed periodic excursions from baseline that corresponded to the cardiac (amplitude, 30-80 µV, lasting 4-5 ms) and respiratory components (amplitude, ~50 µV, lasting ~120 ms). Notably, contained within the signal, there were discrete, aperiodic spikes of variable amplitude that lasted ~2 ms (FIG. 1A). An adaptive threshold technique was used to identify these fast spikes (FIG. 1B) and surmise that they corresponded to compound action potentials (CAPs), which were generated by the near unison firing of multiple axons. To test whether the spikes indeed reflected neuronal activity, nerve activation and inhibition studies were performed. In the former, following baseline acquisition, KCl (4 mM) was applied to the surgical field in close proximity to the vagus nerve so as to depolarize the neural tissue. This treatment produced a significant increase in neural activity (FIG. 1B), with individual CAPs showing large amplitude and stereotypical shape (FIG. 1B). By electrically stimulating the vagus nerve preparation with brief pulses of increasing intensities, evoked CAPs of increasing amplitudes were obtained (FIG. 1C, D). Application of lidocaine, a potent anesthetic that blocks sodium channels, resulted in an almost total disappearance of the evoked CAPs (FIG. 1C). Moreover, application of tetrodotoxin, a highly specific sodium channel blocker, abrogated the evoked CAPs completely (FIG. 1D), corroborating the neural nature of the recordings. Remarkably, inhibition of neural activity did not completely eliminate the cardiac and respiratory components, which were likely a composite of electrocardiac signals, electromyographic signals, and motion artifacts (data not shown).

Afferent nature of the VN neurograms. Examination of baseline vagus nerve activity indicated that anesthetized, unstimulated mice showed minimal activation (FIG. 2A) with an underlying mean CAP frequency of 7.6±1.6 Hz (mean±SEM, N=36 recordings lasting >10 min). Traces were divided into 60-sec intervals, which revealed long periods of complete quiescence (N=85 events with CAP frequency=0) that were punctuated by brief periods of strong neural activity. The CAP frequency distribution for non-silent events was not normally distributed (N=275, P=0, W=0.69, Shapiro-Wilk test), with most events occurring at very low frequency and a few occurring at the high-frequency tail (FIG. 2B). An initial test of the hypothesis that an organism's peripheral inflammatory status may represent a component of the vagus nerve's sensory function was performed by administering TNF (50 µg in 200 µL, i.p.), while continuously recording vagus nerve activity. The resulting post-injection neurogram showed an acute increase in neural activity (FIG. 2A), with a fraction of CAPs occurring at much higher frequency than baseline (FIG. 2B). The enhanced neurogram following TNF administration might reflect sensory signals, motor signals, or even both, traveling through the vagus nerve. To directly test the signal directionality, proximal and distal vagotomies (relative to the brain) were performed prior to administering TNF (FIG. 2C). With a proximal transection, the afferent fibers tracking towards the recording electrodes from the visceral organs remained intact while efferent fibers no longer interface with the electrodes. The opposite was true with the distal vagotomy, in which the recording electrodes no longer accessed afferent fibers but the efferent fibers remained intact. For each experiment, CAPs were identified and the mean CAP frequencies were plotted across recordings (FIG. 2D). To evaluate the responses, 10-min intervals immediately before and after TNF injection were considered. With proximal vagotomy, the CAP frequency showed a significant increase from baseline (pre, 5.8±2.8, post, 39.5±9.1 Hz, mean±SEM). In stark contrast, distal vagotomy resulted in a null enhancement (pre, 5.7±1.3, post, 2.9±1.5 Hz, mean±SEM). Comparison of the individual post-injection CAP frequencies (FIG. 2E) further demonstrated the significant difference between proximal and distal transections (P=0.03, T=3.28, t test). These data indicate that the first response recorded in the cervical vagus nerve neurograms, following cytokine administration, includes and requires the vagus nerve's sensory function.

Figure 3A:
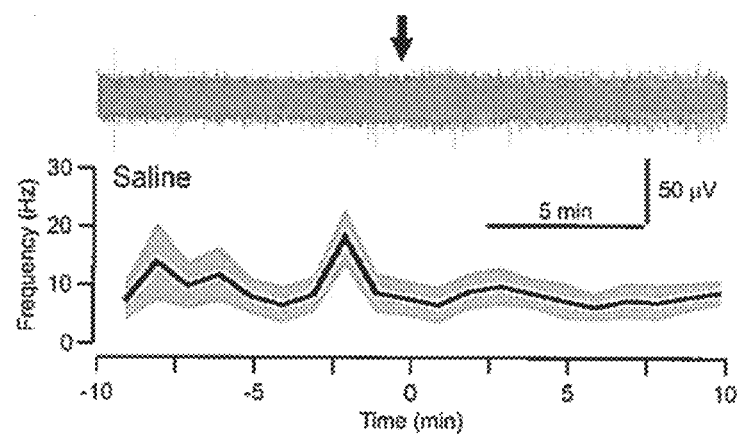
Figure 3B:
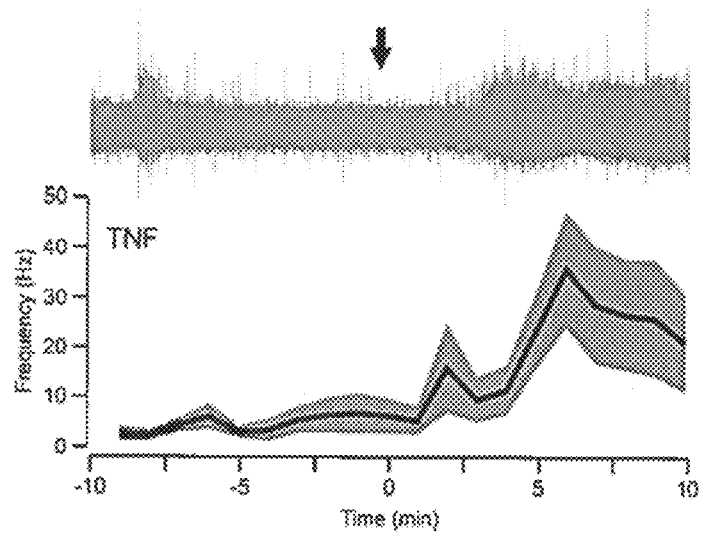

VN neurograms induced by pro-inflammatory cytokines. To further dissect the neural activity associated with inflammatory stimuli, the patterns of responses between TNF and IL-1β were compared using exogenous, purified pro-inflammatory cytokines that were injected into the peritoneal cavity. Saline injection was used as the control (FIG. 3A). Application of TNF (50 μg in 200 μL, i.p.) was followed by a notable increase in activity (FIG. 3B). Analysis of 10-min intervals (immediately before and after TNF) revealed a significantly higher mean CAP frequency after TNF (pre, 4.1±3.7, post, 19.8±4.2 Hz, N=6, P=0.013, U=2, Mann-Whitney [MW] test). The peak CAP frequency, defined as the maximum value within the interval, was also significantly elevated after TNF (pre, 19.8±5.9, post, 69.0±17.8 Hz, N=6, P=0.005, U=0, MW test). Both the initiation and termination of the activity envelopes were rapid, occurring on the order of seconds. Moreover, the period that followed the TNF-induced enhancement had a mean CAP frequency (7.4±4.7 Hz) that was similar to baseline activity.

Figure 3C:
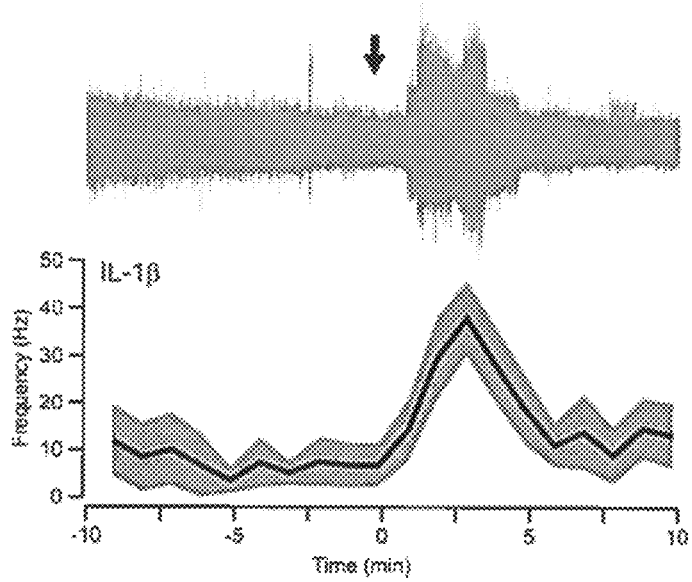

Next, the vagus nerve neurograms were evaluated in the context of injection of IL-1β (350 ng in 200 μL, i.p.). Interestingly, the peak response to IL-1β occurred earlier than that of TNF (FIG. 3C). For this reason, a 5-min interval was used to evaluate the responses immediately before and after injection of IL-1β. The mean CAP frequency was significantly higher following the cytokine (pre, 6.9±3.6, post, 25.5±4.9 Hz, mean±SEM, N=8, P=0.007, U=6, MW test), as well as the peak CAP frequency (pre, 23.9±11.3, post, 74±10.2 Hz, N=8, P=0.013, U=8, MW test). Following the enhanced IL-1β neurogram, the mean CAP frequency returned to baseline level (4.4±1.9 Hz). Importantly, the increased vagus nerve activity that was triggered by cytokines did not reflect physical trauma or disruption to the peritoneal cavity and its viscera because i.p. injection of vehicle alone (200 μL of sterile saline) did not elicit a change in vagus nerve activity (FIG. 3A), as evidenced by the mean CAP frequency (pre, 11.9±4.9, post, 9.6±4.1 Hz, N=5, P=1, U=12, MW test) and the peak frequency (pre, 106.6±23.0, post, 46.0±11.1 Hz, N=5, P=0.037, U=23, MW test).

Figure 3D:
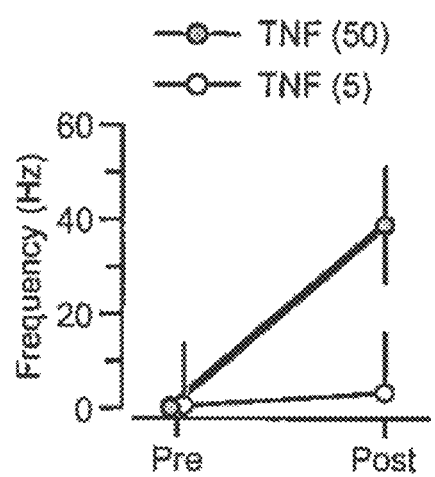
Figure 3E:
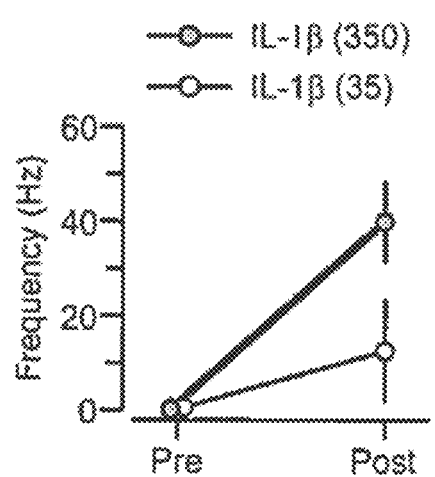

To investigate the dose dependency of the cytokine-induced neurogram enhancement, the amount of administered pro-inflammatory cytokine was titrated. Decreasing the TNF amount ten-fold (5 μg in 200 μL, i.p.) largely abolished the peak response observed 5 min after injecting the higher dose (50 μg) of TNF (FIG. 3D). Similarly, the CAP frequency did not increase in 150 sec following IL-1β administration when it was decreased ten-fold (35 ng in 200 μL, i.p.) (FIG. 3E). The shorter time intervals used for IL-1β compared with TNF reflected the different temporal profiles of neurogram activation to IL-1β compared with TNF. In particular, the IL-1β response peaked earlier (150 sec post-injection) as compared with TNF (300 sec post-injection).

Differences between neurograms induced by TNF and IL-1β. Comparison of the mean CAP frequencies (FIG. 4A), pre- and post-treatment, revealed significant differences between the saline, TNF and IL-1β groups (P=0.0125, F [2, 21]=5.57, one-way ANOVA). Post-hoc tests also showed that the TNF and IL-1β values were each significantly different to saline (TNF, P=0.006, U=2; IL-1β, P=0.01, U=7, MW test). However, there was no difference between the pro-inflammatory cytokines (P=0.65, U=20, MW test). Analysis of the peak CAP frequency (FIG. 4B), pre- and post-treatment, showed a statistical significance between the three groups (P=6.5×10-4, F [2, 21]=11.07, ANOVA). Post-hoc tests also demonstrated that the TNF and IL-1β peak responses were each significantly different from saline (TNF, P=0.002, U=0; IL-1β, P=0.003, U=3, MW test). Additionally, the peak CAP frequency changes between pro-inflammatory cytokines were not significantly different (P=0.95, U=23, MW test). The temporal profiles of neurogram activation with TNF and IL-1β treatments were compared by defining the beginning of the response as the time at which the CAP frequency increased to 3× the pre-injection rate, and the response termination as the time when the frequency decreased below the same value. Using these definitions, the latency, duration, and mean CAP frequency for the responses were analyzed (FIG. 4C). The neurograms induced by TNF (N=6) and IL-1β (N=7) had different latencies (TNF, 156.2±40.4, IL-1β, 47.6±15.2 sec, P=0.043, T=2.52, t test). In contrast, the response duration (TNF, 185.2±47.2, IL-1β, 222.6±73.8 sec, P=0.68, T=0.43, t test) and mean CAP frequency (TNF, 35.92±5.2, IL-1β, 42.7±4.6 Hz, P=0.35, T=0.97, t test) were not different.

Receptor requirement for the neurograms induced by TNF and IL-1β. It has previously been demonstrated that TNF trimers can form receptor-independent transmembrane channels (19). In this case, the administration of TNF could in theory directly activate neurons without engaging its receptor. To test whether the cytokine-induced responses required cytokine-receptor signaling, the vagus nerve neurograms from receptor knockout (KO) mice were recorded. TNF injection in TNFR2 KO mice did not lead to a change in the neurogram (FIG. 5A), implicating a ligand-receptor interaction in the observed response enhancement. Next, the requirement for the IL-1β receptor (IL-1R) in the IL-1β-induced neurogram activation was tested. Exogenous IL-1β did not stimulate the cervical vagus nerve in IL-1R KO mice (FIG. 5B). In all KO mouse experiments in which no clear response was observed, KCl (4 mM) was applied to the nerve at the termination of the experiments to ensure vagus nerve viability (data not shown). Additionally, in complementary cross-over studies, i.p. administration of IL-1 in TNFR1/R2 double KO mice did induce an increase in vagus nerve signaling (data not shown). Similarly, IL-1R KO mice responded to i.p. administration of TNF with increased vagus nerve activity (data not shown).

To test the requirement of full length TNF for vagal nerve activation, recombinant human TNF was digested in 0.05% trypsin overnight at 37 deg C. The trypsin was heat-inactivated by incubating the solution at 95 deg C. for 7 min. A digestion of approximately 90% was confirmed by SDS-PAGE gel. Digested or full-length TNF (50 μg/animal) was injected into the peritoneum while continuously recording from the cervical vagus nerve. As expected, trypsin-digested TNF did not reproduce the effects of full-length TNF on vagal nerve activation (data not shown).

Spectral power of the VN signals induced by TNF and IL-1β. Given that TNF and IL-1β elicit similar, but not identical, enhancements in the vagus nerve neurograms and that these cytokine receptor-dependent signals involved afferent fibers, it was examined whether the vagus nerve is capable of sending distinct signals about TNF and IL-1β to the CNS. To investigate this possibility, the power spectral densities (PSDs) of the TNF and IL-1β responses were analyzed, using unfiltered neurogram recordings. As above, the response was defined as the first interval of time in which the CAP frequency resided at 3× the baseline level. Representative PSDs for TNF and IL-1β are shown in FIG. 6A. Next, each filtered PSD was integrated (from 20 to 400 Hz) to compare the individual areas of the TNF and IL-1β responses (FIG. 6B). Statistical analysis revealed a significant difference between TNF and IL-1β groups (N=7, P=0.05, D=0.71, Kolmogorov-Smirnov test). Together, the difference in the response temporal characteristics and frequency domain power analyses indeed demonstrated a selective cytokine neural sensory signaling through the vagus nerve.

Discussion

The work presented here adds to the rapidly expanding literature describing the interface between neuroscience and immunology, delineating for the first time the afferent arc of the inflammatory reflex. Use of surgical vagotomies verified the postulate that afferent fibers of the vagus nerve can function as cytokine sensors that relay information to the CNS (5-7). Moreover, analysis of neurograms for TNF and IL-1β reveal selective, specific, afferent signaling of the vagus nerve in response to respective pro-inflammatory cytokines.

At the cellular level, the mechanism by which systemic cytokines elicit neuronal activation in the vagus nerve remains an active area of research. Several studies have demonstrated the presence of functional cytokine receptors within neuronal populations, such that activation of these receptors is capable of modulating neuronal excitability (10-12). A recent report has shown that bacterial products can directly activate a specific population of sensory neurons (13). It follows that the pro-inflammatory cytokines may directly activate sensory vagus nerve fibers within the peritoneum. Alternatively, intermediate populations of receptor-expressing somatic cells may be required to sense the cytokine and, in turn, stimulate the neurons.

Remarkably, the differences between TNF and IL-1β indicate that the CNS can discriminate between a diverse set of inflammatory mediators. This notion has a strong teleological basis because the CNS receives a continuous sensory flow pertaining to the internal body environment, of which the signals that relay systemic inflammation must constitute a key element for an animal's homeostasis and survival. With the rapid delivery of signals on peripheral inflammatory (and immune) status, an organism would be better able to initiate appropriate physiological and behavioral responses to immunological and environmental challenges.

In addition to the observed temporal differences in neurogram enhancement between TNF and IL-1β, the spectral densities of the individual responses (FIG. 5) provide further evidence for the existence of discriminating features between the cytokine-elicited vagus nerve activities that could be interpreted by CNS centers, such as the nucleus tractus solitarius. There is ample evidence that many cortical and subcortical structures within the CNS can distinguish the spectral characteristics of signals and use them in processes as diverse as memory encoding, decision making, and switching between sleep states (14-16). Either alone or in combination, the observed differences in time and frequency domain metrics may represent the biological substrate for the discrimination of peripheral cytokines by the CNS.

The interface between neuroscience, immunology, and clinical medicine is increasingly moving to the fore, especially as the use of electrical devices as therapeutic agents for disease becomes a reality and shapes the emerging field of bioelectronic medicine (17). For instance, a recent clinical trial that used vagus nerve stimulation to treat rheumatoid arthritis proved successful (18).

Example 2. Delivering Cytokine Specific Codes to Naïve Animals by Electrical Vagus Nerve Stimulation using Cytokine-Specific Neurograms Recorded from the Afferent Vagus Nerve The cervical vagus nerve was stimulated in naïve animals using cytokine-specific codes, and the resulting effects were correlated with physiological endpoints.

Baseline controls and signals in response to i.p. IL-1β injection were obtained from the vagus nerve of one mouse. The nerve recordings were high-pass filtered (w/160 Hz edge) and converted to .wav format. Hook stimulating electrodes were placed on the cervical vagus nerve of a second mouse. The IL-1β cytokine signal was delivered to the second mouse using an analog stimulus isolator (Model 2200, A-M Systems). A 1 mA/V setting was used. The amplitude of the output was calibrated using a sample single frequency file. This file was played and the output of the computer was set so that the amplitude of output was ±5V (10 V p-p). A 1 kΩ resistor was added to optimize the impedance. Serum cytokine levels were measured 1 hr post-stimulation.

Stimulating the vagus nerve of a naïve mouse with IL1-specific neural code recapitulates the IL1-induced inflammatory phenotype as reflected in serum levels of interleukin-6 (IL-6) and interleukin-8 (IL-8) (FIG. 7).

As a control, the IL1β-specific signal was transformed to a scrambled signal using a Matlab code that generates a randomized signal with the same amplitudes, but random frequencies maintaining the total power of the signal. The scrambled signal was transferred to a naïve receiver mouse using an analog stimulator isolator. Stimulating the vagus nerve of the naïve mouse with a scrambled interleukin-1 beta (IL-1β) control stimulus pattern had no effect on measured serum cytokine levels (FIG. 8).

Example 3. Neurograms Specific for Anti-Inflammatory/Stress Conditions

Naïve mice received a bolus of the anti-inflammatory cytokine IL-10 (1 μg/mouse), and vagus nerve activity was recorded over time. An IL-10-induced neurogram was recorded from the cervical vagus nerve (FIG. 9).

Similarly, a hydrocortisone-induced neurogram was recorded from the cervical vagus nerve of naïve mice that received a bolus of hydrocortisone (cortisol) (10 mg/mouse) (FIG. 10).

Example 4. Induction of Anti-Inflammatory Phenotype in Naïve Mice Using Cortisol-Specific Neurogram Signal Transfer by Electric Stimulation of the Cervical Vagus Nerve A cortisol-specific signal was extracted from a neurogram obtained from one mouse (mouse A in FIG. 11). The nerve recordings were high-pass filtered (w/160 Hz edge) and converted to .wav format. For a control signal, the cortisol-specific signal from mouse A was transformed to a scrambled signal using a Matlab code that generates a randomized signal with the same amplitudes, but random frequencies while maintaining the total power of the signal. The cervical vagus nerve was isolated from another naïve receiver mouse (mouse B in FIG. 11) and placed on hook stimulating electrodes. The cortisol-specific or scrambled signal was transferred to receiver mouse B using an analog stimulator isolator (Model 2200, A-M Systems). Serum IL-10 levels were monitored in mouse B at regular time intervals. Stimulation of the cervical vagus nerve of the naïve mouse with the cortisol-specific signal induced an increase in serum levels of the anti-inflammatory cytokine IL-10 (FIG. 12). Stimulation of the vagus nerve using the control scrambled signal did not induce an increase in serum IL-10 levels (FIG. 12).

Example 5. Attenuation of Endotoxin-Induced Inflammatory Response in Naïve Mice by Transferring a Dexamethasone-Specific Neurogram A dexamethasone (dex)-specific signal was extracted from a neurogram obtained from mouse A. The cervical vagus nerve was isolated from a naïve receiver mouse B and placed on a stimulating electrode. A scrambled dex signal was used as the control. Either dex or scrambled signal was transferred using an analog stimulator isolator to receiver mouse B. Animals were challenged with 0.1 mg/kg endotoxin 24 hrs post-stimulation. TNF levels were analyzed in receiver mice after 90 min. Simulation of the vagus nerve with the dex-specific signal attenuated TNF levels (FIG. 13).

Example 6. Vagus Neurograms Specific for Euglycemia, Hyperglycemia and Hypoglycemia Conditions Recording of hypoglycemic neurogram. Naïve mice received a bolus of insulin (6 mg/kg), and vagus nerve activity was recorded over time (FIG. 14). The blood glucose levels were monitored after every 2.5 min. Insulin induced a hypoglycemic condition in mice. Blood glucose levels are indicated in the top line of FIG. 14 in mg/dL.

Recording of euglycemic neurogram. Naïve mice received a bolus of glucagon (1 mg/kg), and vagus nerve activity was recorded over time (FIG. 15). The blood glucose levels were monitored after every 2.5 min. Blood glucose levels are indicated in the top line of FIG. 11 in mg/dL.

Recording of hyperglycemic neurogram. Naïve mice received a bolus of glucose, and vagus nerve activity was recorded over time (FIG. 16). The blood glucose levels were monitored after every 2.5 min. Glucose induced a hyperglycemic condition in mice. Blood glucose levels are indicated in the top line of FIG. 16 in mg/dL.

Example 7. Induction of Hypoglycemic Phenotype in Naïve Mice Using Hypogycemic-Specific Neurogram Signal Transfer by Electric Stimulation of the Cervical Vagus Nerve Baseline or hypoglycemia-specific signals were extracted from neurograms obtained from one mouse (mouse A in FIG. 17). The cervical vagus nerve was isolated from a naïve receiver mouse (mouse B in FIG. 17) and placed on stimulating hook electrodes. The baseline or hypoglycemia-specific signal from mouse A was transferred using an analog stimulator isolator to the cervical vagus nerve of receiver mouse B. Blood glucose levels were monitored in mouse B at regular time intervals. Direct electric playback of the hypoglycemia-specific neurogram induced hypoglycemia in mice (FIG. 18). In contrast, stimulating the vagus nerve of naïve mouse with a random insulin control stimulus pattern or a baseline signal had no effect on blood glucose levels (FIGS. 19-21). Vagus nerve stimulation with the hypoglycemia-specific neurogram did not cause a significant change in circulating levels of glucagon, insulin or c-peptide (FIG. 22). Thus, the changes in blood glucose levels are independent of circulating levels of glucagon, insulin or c-peptide.

Hypoglycemia induced by vagal stimulation with an insulin stimulus pattern requires afferent vagal signaling to the brain (FIG. 23A-23C). Blockade of the vagus nerve with lidocaine was performed proximal or distal to the stimulating site. Animals with proximal vagal blockade did not respond to stimulation. In contrast, animals with distal vagal blockade did respond to stimulation. Serum insulin (upper) and c-peptide (lower) levels were not significantly different. In contrast to vagal afferent mediation of the hypoglycemic effect induced by the insulin stimulus pattern, electrical stimulation of vagal efferents using pulses has been shown to elicit anti-inflammatory effects (20, 21).

FIG. 24 illustrates the effects of vagus nerve stimulation with an insulin stimulus pattern or a random signal on levels of circulating leptin and glucagon-like peptide-1 (GLP-1). The hypoglycemic effect induced by electrical stimulation of the vagus nerve with the insulin stimulus pattern requires leptin signaling, as demonstrated in leptin- and leptin receptor-knockout animals (FIG. 25-26).

The transient receptor potential cation channel subfamily V member 1 (TRPV1) plays an inhibitory role on the circuit used to lower glucose in the insulin resistant state (FIGS. 27-29). TRPV1 is also known as the capsaicin receptor and the vanilloid receptor 1.

Example 8. Induction of Hypoglycemia in Naïve Mice Using Cortisol-Specific Neurogram Signal Transfer by Electric Stimulation of the Cervical Vagus Nerve Administration of cortisol induces hypoglycemia in mice. Naïve mice received either saline or cortisol by intraperitoneal administration. Blood glucose levels were monitored over time. Cortisol but not saline administration induced hypoglycemia (FIG. 30).

Playback of cortisol-specific neurogram by direct nerve stimulation of the cervical vagus nerve induces hypoglycemia. Naïve receiver mice received either scrambled or cortisol-specific neurogram signal (FIG. 10, 11) by direct electrical activation of the cervical vagus nerve. Blood glucose levels were monitored. The cortisol-specific signal but not the scrambled signal induced hypoglycemia (FIG. 31).

REFERENCES

1. Blalock J E (1984) The immune system as a sensory organ. *J Immunol* 132(3):1067-70.
2. Tracey K (2002) The inflammatory reflex. *Nature* 420 (6917):853-859.
3. Rosas-Ballina M et al. (2011) Acetylcholine-synthesizing T cells relay neural signals in a vagus nerve circuit. *Science* 334(6052):98-101.
4. Reardon C et al. (2013) Lymphocyte-derived ACh regulates local innate but not adaptive immunity. *Proc Natl Acad Sci USA* 110(4):1410-1415.
5. Niijima A, Hori T, Katafuchi T, Ichijo T (1995) The effect of interleukin-1 beta on the efferent activity of the vagus nerve to the thymus. *J Auton Nerv Syst* 54(2):137-144.
6. Niijima A (1996) The afferent discharges from sensors for interleukin 1 beta in the hepatoportal system in the anesthetized rat. *J Auton Nerv Syst* 61(3):287-291.

7. Niijima A (1992) Electrophysiological study on the vagal innervation of the adrenal gland in the rat. *J Auton Nerv Syst* 41(1-2):87-92.
8. Hansen M, O'Connor K, Goehler L, Watkins L, Maier S (2001) The contribution of the vagus nerve in interleukin-1beta-induced fever is dependent on dose. *Am J Physiol Regul Integr Comp Physiol* 280(4):R929-934.
9. Watkins L et al. (1995) Blockade of interleukin-1 induced hyperthermia by subdiaphragmatic vagotomy: evidence for vagal mediation of immune-brain communication. *Neurosci Lett* 183 (1-2): 27-31.
10. Czeschik J, Hagenacker T, Schäfers M, Büsselberg D (2008) TNF-α differentially modulates ion channels of nociceptive neurons. *Neurosci Lett* 434(3):293-298.
11. Hagenacker T, Czeschik J, Schäfers M, Büsselberg D (2010) Sensitization of voltage activated calcium channel currents for capsaicin in nociceptive neurons by tumor-necrosis-factor-α. *Brain Res Bull* 81(1): 157-163.
12. Binshtok A et al. (2008) Nociceptors are interleukin-1beta sensors. *J Neurosci* 28(52): 14062-14073.
13. Chiu I et al. (2013) Bacteria activate sensory neurons that modulate pain and inflammation. *Nature* 501(7465): 52-57.
14. Buzsáki G, Moser E I (2013) Memory, navigation and theta rhythm in the hippocampal-entorhinal system. *Nat Neurosci* 16(2): 130-138.
15. Nácher V, Ledberg A, Deco G, Romo R (2013) Coherent delta-band oscillations between cortical areas correlate with decision making. *Proc Natl Acad Sci USA* 110(37): 15085-15090.
16. Kopell N, Kramer M A, Malerba P, Whittington M A (2010) Are different rhythms good for different functions? *Front Hum Neurosci* 4:187. doi: 10.3389/fnhum.2010.00187.
17. Famm K, Litt B, Tracey K, Boyden E, Slaoui M (2013) Drug discovery: a jump-start for electroceuticals. *Nature* 496(7444): 159-161.
18. Koopman F A et al. (2012) Pilot study of stimulation of the cholinergic anti-inflammatory pathway with an implantable vagus nerve stimulation device in patients with rheumatoid arthritis. *Arthritis Rheum* 64(10 Sunni): S195.
19. Kagan B L, Baldwin R L, Munoz D, Wisnieski B J (1992) Formation of ion-permeable channels by tumor necrosis factor-alpha. *Science* 255(5050):1427-1430.
20. Borovikova L V, Ivanova S, Zhang M, Yang H, Botchkina G I, Watkins L R, Wang H, Abumrad N, Eaton J W, Tracey K J (2000) Vagus nerve stimulation attenuates the systemic inflammatory response to endotoxin. *Nature* 405(6785):458-62.
21. Olofsson P S, Levine Y A, Caravaca A, Chavan S S, Pavlov V A, Faltys M, Tracey K J (2015) Single-pulse and unidirectional electrical activation of the cervical vagus nerve reduces tumor necrosis factor in endotoxemia. *Bioelectronic Medicine* 2:37-42.

What is claimed is:

1. A method for treating a subject having a disease or disorder comprising electrically stimulating a nerve of the subject with a corrective stimulus pattern derived from a previously recorded disease-specific, condition-specific, endogenous mediator-specific or pharmacologic agent-specific neurogram in an amount and manner effective to treat the disease or disorder;
wherein the disease or disorder is one or more of inflammation, type 1 diabetes, type 2 diabetes, metabolic syndrome, insulin resistance, glucose intolerance, hyperglycemia, hypoglycemia, trauma, bleeding, hemorrhagic shock, ischemia-reperfusion injury, nausea, vomiting, cancer, prostate cancer, arthritis, rheumatoid arthritis, sepsis, endotoxemia, colitis, pancreatitis, inflammatory bowel disease, Crohn's Disease, fever, anorexia, pain, swelling, kidney failure, liver disease, hypothyroidism, a host response to infection, an immune response, and a disease or disorder in which it is desirable to change the activity or level of a cytokine;
wherein the disease-specific, condition-specific, endogenous mediator-specific or pharmacologic agent-specific neurogram is previously recorded from a vagus nerve, splenic nerve, splanchnic nerve, sciatic nerve, or a nerve to a specific organ or portion of an organ using an animal model of the disease or disorder, or from a human patient; and
wherein corrective stimulus pattern is applied electrically to a vagus nerve, splenic nerve, splanchnic nerve, sciatic nerve, or a nerve to a specific organ or portion of an organ of the subject.

2. The method of claim 1, wherein a previously recorded neurogram is obtained in response to administration of a physiologically occurring substance to the animal model or to the human patient.

3. The method of claim 1, wherein a previously recorded neurogram is obtained in response to administration of a cytokine or administration of glucagon, glucose or insulin to the animal model or to the human patient.

4. The method of claim 1, wherein the corrective stimulus pattern is derived from a previously recorded cytokine-specific neurogram previously recorded from the vagus nerve of the animal model or from the vagus nerve of the human patient.

5. The method of claim 1; for controlling blood glucose levels in a subject, the method comprising electrically stimulating a cervical vagus nerve of the subject with a corrective stimulus pattern derived from a previously recorded hypoglycemic- or hyperglycemic-specific neurogram previously recorded from a vagus nerve in an amount and manner effective to control blood glucose levels in a subject.

6. The method of claim 5; for decreasing blood glucose levels in a subject comprising electrically stimulating a cervical vagus nerve of the subject with a corrective stimulus pattern derived from a previously recorded hypoglycemic-specific, insulin-specific or cortisol-specific neurogram previously recorded from a vagus nerve in an amount and manner effective to decrease blood glucose levels in a subject.

7. The method of claim 1, wherein a cervical vagus nerve is electrically stimulated with a corrective stimulus pattern derived from a previously recorded cortisol-specific neurogram previously recorded from the vagus nerve of the animal model or from the vagus nerve of the human patient.

8. The method of claim 1; for treating a subject having inflammation, the method comprising electrically stimulating a cervical vagus nerve of the subject with a corrective stimulus pattern derived from a previously recorded anti-inflammatory cytokine-specific or cortisol-specific or dexamethasone-specific neurogram previously recorded from a vagus nerve in an amount and manner effective to treat inflammation in a subject.

9. The method of claim 8, wherein an anti-inflammatory cytokine is selected from the group consisting of interleukin-4 (IL-4), interleukin-6 (IL-6), interleukin-10 (IL-10), interleukin-11 (IL-11), interleukin-13 (IL-13) and interleukin-35 (IL-35).

10. The method of claim 8, wherein a cervical vagus nerve is electrically stimulated with a corrective stimulus pattern derived from a previously recorded cortisol-specific neurogram previously recorded from the vagus nerve of the animal model or from the vagus nerve of the human patient.

11. The method of claim 8, wherein a cervical vagus nerve is electrically stimulated with a corrective stimulus pattern derived from a previously recorded dexamethasone-specific neurogram previously recorded from the vagus nerve of the animal model or from the vagus nerve of the human patient.

12. The method of claim 8, wherein electrically stimulating a cervical vagus nerve of the subject with the corrective stimulus pattern decreases serum levels of one or more inflammatory cytokines selected from the group consisting of interleukin-1β (IL-1β) and tumor necrosis factor (TNF).

13. The method of claim 1, wherein the infection is a bacterial infection.

14. The method of claim 1, wherein the corrective stimulus pattern is applied to the vagus nerve and wherein physiologic effects of the corrective stimulus pattern are mediated by vagus nerve afferents.

15. The method of claim 1, wherein nerve recording and/or nerve stimulation are carried out using implantable electrodes.

16. A method for generating a corrective stimulus for the treatment of a disease or condition in a first subject, the method comprising the steps of:
    providing a previously recorded disease-specific, condition-specific, endogenous mediator-specific or pharmacologic agent-specific neurogram previously recorded from a second subject, and
    generating a corrective neural stimulus based therefrom;
    wherein the disease or disorder is one or more of inflammation, type 1 diabetes, type 2 diabetes, metabolic syndrome, insulin resistance, glucose intolerance, hyperglycemia, hypoglycemia, trauma, bleeding, hemorrhagic shock, ischemia-reperfusion injury, nausea, vomiting, cancer, prostate cancer, arthritis, rheumatoid arthritis, sepsis, endotoxemia, colitis, pancreatitis, inflammatory bowel disease, Crohn's Disease, fever, anorexia, pain, swelling, kidney failure, liver disease, hypothyroidism, a host response to infection, an immune response, and a disease or disorder in which it is desirable to change the activity or level of a cytokine; and
    wherein the disease-specific, condition-specific, endogenous mediator-specific or pharmacologic agent-specific neurogram is previously recorded from a vagus nerve, splenic nerve, splanchnic nerve, sciatic nerve, or a nerve to a specific organ or portion of an organ of the second subject, wherein the second subject is an animal model of the disease or disorder, or a human patient.

17. The method of claim 16, wherein a previously recorded neurogram is previously recorded in response to administration of a physiologically occurring substance to the second subject.

18. A method for treating a first subject having a disease or disorder comprising electrically stimulating a nerve of the first subject with a corrective stimulus pattern derived from a previously recorded disease-specific, condition-specific, endogenous mediator-specific or pharmacologic agent-specific neurogram previously recorded from a second subject, wherein electrically stimulating the nerve of the first subject is in an amount and manner effective to treat the disease or disorder;
    wherein the disease or disorder is one or more of inflammation, type 1 diabetes, type 2 diabetes, metabolic syndrome, insulin resistance, glucose intolerance, hyperglycemia, hypoglycemia, trauma, bleeding, hemorrhagic shock, ischemia-reperfusion injury, nausea, vomiting, cancer, prostate cancer, arthritis, rheumatoid arthritis, sepsis, endotoxemia, colitis, pancreatitis, inflammatory bowel disease, Crohn's Disease, fever, anorexia, pain, swelling, kidney failure, liver disease, hypothyroidism, a host response to infection, an immune response, and a disease or disorder in which it is desirable to change the activity or level of a cytokine;
    wherein the disease-specific, condition-specific, endogenous mediator-specific or pharmacologic agent-specific neurogram is previously recorded from a vagus nerve, splenic nerve, splanchnic nerve, sciatic nerve, or a nerve to a specific organ or portion of an organ of the second subject, wherein the second subject is an animal model of the disease or disorder, or a human patient; and
    wherein corrective stimulus pattern is applied electrically to a vagus nerve, splenic nerve, splanchnic nerve, sciatic nerve, or a nerve to a specific organ or portion of an organ of the first subject.

19. The method of claim 18, wherein the previously recorded neurogram is obtained in response to administration of a physiologically occurring substance to the second subject.

* * * * *